(12) United States Patent
Wyss-Coray et al.

(10) Patent No.: US 8,097,645 B2
(45) Date of Patent: Jan. 17, 2012

(54) COMPOUNDS FOR ACTIVATING TGF-β SIGNALING

(75) Inventors: Anton Wyss-Coray, Stanford, CA (US); Mary J. Tanga, Los Alto, CA (US)

(73) Assignees: The Board of Trustees of the Leland Stanford Junior University, Stanford, CA (US); SRI International, Menlo Park, CA (US)

( * ) Notice: Subject to any disclaimer, the term of this patent is extended or adjusted under 35 U.S.C. 154(b) by 330 days.

(21) Appl. No.: 12/249,577

(22) Filed: Oct. 10, 2008

(65) Prior Publication Data

US 2009/0143394 A1   Jun. 4, 2009

Related U.S. Application Data

(60) Provisional application No. 60/998,658, filed on Oct. 12, 2007.

(51) Int. Cl.
*A01N 43/38* (2006.01)
*A61K 31/40* (2006.01)
*A61K 31/405* (2006.01)
*C07D 209/02* (2006.01)

(52) U.S. Cl. .................... 514/415; 514/419; 548/466
(58) Field of Classification Search ............... 548/466; 514/415, 419
See application file for complete search history.

(56) References Cited

FOREIGN PATENT DOCUMENTS
WO   WO 2005/056012 A1   6/2005

OTHER PUBLICATIONS

XP-002521233, Aug. 2005.*
XP-002521234, Aug. 2005.*
XP-002521235, Aug. 2005.*
XP-002521247, Aug. 2005.*
Massague, et al., Cell 103, 295-309 (2000).*
Dennler, et al., J. Leukoc. Biol. 71, 731-40 (2002).*
Lutz, et al., Cell Signal 14, 977-88 (2002).*
Albany Molecular Research Inc., Database Chemcats [Online], Chemical Abstract Service, Columbus, Ohio, XP002521243, Database Accession No. 2066786696 (2009).
Albany Molecular Research Inc., Database Chemcats [Online], Chemical Abstract Service, Columbus, Ohio, XP002521248, Database Accession No. 2066348893 (2009).
Albany Molecular Research Inc., Database Chemcats [Online], Chemical Abstract Service, Columbus, Ohio, XP002522130, Database Accession No. 2066545700 (2009).
Albany Molecular Research Inc., Database Chemcats [Online], Chemical Abstract Service, Columbus, Ohio, XP002518339, Database Accession No. 1024194-68-0 (2008).
Albany Molecular Research Inc., Database Chemcats [Online], Chemical Abstract Service, Columbus, Ohio, XP002521231130, Database Accession No. 2066546596 (2009).
ComGenex International Inc., Database Registry [Online], Chemical Abstract Service, Columbus, Ohio, XP002521232, Database Accession No. 861980-61-2 (2005).
ComGenex International Inc., Database Registry [Online], Chemical Abstract Service, Columbus, Ohio, XP002521233, Database Accession No. 861987-78-2 (2005).
ComGenex International Inc., Database Registry [Online], Chemical Abstract Service, Columbus, Ohio, XP002521234, Database Accession No. 861983-58-6 (2005).
ComGenex International Inc., Database Registry [Online], Chemical Abstract Service, Columbus, Ohio, XP002521235, Database Accession No. 861992-94-1 (2005).
ComGenex International Inc., Database Registry [Online], Chemical Abstract Service, Columbus, Ohio, XP002521236, Database Accession No. 861984-82-9 (2005).
ComGenex International Inc., Database Registry [Online], Chemical Abstract Service, Columbus, Ohio, XP002521237, Database Accession No. 861985-40-2 (2005).
ComGenex International Inc., Database Registry [Online], Chemical Abstract Service, Columbus, Ohio, XP002521238, Database Accession No. 853611-03-7 (2005).
ComGenex International Inc., Database Registry [Online], Chemical Abstract Service, Columbus, Ohio, XP002521240, Database Accession No. 859384-35-3 (2005).
ComGenex International Inc., Database Registry [Online], Chemical Abstract Service, Columbus, Ohio, XP002521241, Database Accession No. 859457-39-9 (2005).
ComGenex International Inc., Database Registry [Online], Chemical Abstract Service, Columbus, Ohio, XP002521242, Database Accession No. 861982-90-3 (2005).
ComGenex International Inc., Database Registry [Online], Chemical Abstract Service, Columbus, Ohio, XP002521244, Database Accession No. 861708-37-4 (2005).
ComGenex International Inc., Database Registry [Online], Chemical Abstract Service, Columbus, Ohio, XP002521245, Database Accession No. 861994-60-7 (2005).
ComGenex International Inc., Database Registry [Online], Chemical Abstract Service, Columbus, Ohio, XP002521246, Database Accession No. 861981-74-0 (2005).
ComGenex International Inc., Database Registry [Online], Chemical Abstract Service, Columbus, Ohio, XP002521247, Database Accession No. 861981-46-6 (2005).
ComGenex International Inc., Database Registry [Online], Chemical Abstract Service, Columbus, Ohio, XP002521249, Database Accession No. 861989-58-4 (2005).
Inetrnational Search Report and Written Opinion for PCT/US2008/011648, 21 pages, search report dated Jun. 29, 2009.
CAS Registry No. 853145-94-5, American Chemical Society (STN) (2005).
CAS Registry No. 853118-82-8, American Chemical Society (STN) (2007).
CAS Registry No. 860074-75-5, American Chemical Society (STN) (2007).
Glaser K.B. et al., "Transforming growth factor beta mimetics: discovery of 7-[4-(4-cyanophenyl)phenoxy]-heptanohydroxamic acid, a biaryl hydroxamate inhibitor of histone deacetylase", *Molecular Cancer Therapeutics*, 1:759-768 (2002).

* cited by examiner

*Primary Examiner* — Andrew D Kosar
*Assistant Examiner* — Erich A Leeser
(74) *Attorney, Agent, or Firm* — King & Spalding LLP; Stephen Todd; Susan T. Evans

(57) ABSTRACT

Compositions and methods for treatment and prevention of disorders and conditions characterized by reduced TGF-β signaling are described.

13 Claims, 12 Drawing Sheets

A

B

A

Region A

Region C

Region B

B

COMPOUNDS FOR ACTIVATING TGF-β SIGNALING

PRIORITY

The present application claims priority to U.S. Provisional Application Ser. No. 60/998,658, filed Oct. 12, 2007, which is herein incorporated by reference in its entirety.

FEDERALLY-SPONSORED RESEARCH OR DEVELOPMENT

This invention was made with Government support from the Department of Veterans Affairs and under contract AG020603 awarded by the National Institutes of Health. The Government has certain rights in this invention.

TECHNICAL FIELD

The present subject matter relates to small-molecule compositions and methods for treatment and prevention of diseases and conditions associated with reduced TGF-β signaling, including neurological disorders.

BACKGROUND

TGF-β

Transforming growth factor-β (TGF-β) signaling is implicated in a numerous diseases and conditions, including stroke, heart disease, bone loss, cancer, multiple sclerosis, wound healing, inflammation, and neurodegenerative disorders. TGF-β is a member of a superfamily of conserved cytokines, growth factors, and morphogens, which play key functions in development and homeostasis.[9-11] The TGF-β subfamily includes three isoforms in mammals, TGF-β1, 2 and 3, which promote cell survival, induce apoptosis, stimulate cell proliferation, induce differentiation, and/or initiate or resolve inflammation, depending on the particular cell type and environment. Accurate regulation of TGF-β bioactivity and signaling is key to controlling these functions and essential to health and normal aging. The disruption of TGF-β signaling molecules frequently results in embryonic lethality in mice.[12,13]

The biological actions of TGF-βs are mediated by a receptor complex consisting of the TGF-β type 1 (TBR1/ALK5) and type 2 (TBR2) serine/threonine kinase receptor subunits.[9,10] Receptor activation leads to phosphorylation of Smad proteins, which translocate to the nucleus where they bind to the Smad DNA-binding element (SBE) present in an estimated 400 genes.[14] TGF-βs can also activate other signaling pathways including the p38 MAP kinase pathway and the JNK or NF-kB pathways.[11] Despite interaction with other pathways, knockout studies in mice suggest that Smad proteins are the key mediators of many of TGF-β1's actions in vivo.[13]

TGF-B in the CNS

TGF-β is known to play a role in neurological diseases and condition. In the normal central nervous system (CNS), TGF-β1, 2, and 3, and their receptors are expressed in neurons, astrocytes, and microglia.[4,5] The best studied isoform, TGF-β1, is expressed in the adult CNS predominantly in response to CNS injury, and may function as an organizer of protective and regenerative responses.[15] It is upregulated in glial cells in response to brain lesioning, transient forebrain ischemia, and stroke.[5] TGF-β2 and TGF-β3 bind to the same receptors as TGF-β1 but have different patterns of activation and expression.[10,16] Immunoreactivity to TGF-β2 and TGF-β3 is detected in astrocytes and neurons in the normal CNS and is increased in neurodegenerative diseases or after stroke.[4,5] Changes in TGF-β expression are reported in AD brain, cerebrospinal fluid (CSF), and serum.[3,17-22] TGF-β1 immunoreactivity is increased in (or near) amyloid plaques[19,20] and around cerebral blood vessels.[3,18,22]

TGF-β Protection of Neurons

TGF-β1 has been demonstrated to protect neurons against various toxins and injurious agents in cell culture and in vivo.[4,5,32] Astroglial overexpression of TGF-β1 in transgenic mice protected against neurodegeneration induced with the acute neurotoxin kainic acid or associated with chronic lack of apolipoprotein E expression.[7] Boche and coworkers also demonstrated that TGF-β1 protects neurons from excitotoxic death.[36]

Several mechanisms have been postulated to explain how TGF-β1 protects neurons. For example, TGF-β1 decreases Bad, a pro-apoptotic member of the Bcl-2 family, and contributes to the phosphorylation, and thus inactivation, of Bad by activation of the Erk/MAP kinase pathway.[37] On the other hand, TGF-β1 increases production of the anti-apoptotic protein Bcl-2.[38] TGF-β1 has also been shown to synergize with neurotrophins and/or be necessary for at least some of the effects of a number of important growth factors for neurons, including neurotrophins, fibroblast growth factor-2, and glial cell-line derived neurotrophic factor.[32,39] In addition, TGF-β1 increases laminin expression[40] and is necessary for normal laminin protein levels in the brain.[7] It is also possible that TGF-β1 decreases inflammation in the infarction area, attenuating secondary neuronal damage.[35]

Transgenic Animals

TGF-β1 transgenic mice overexpressing a secreted, constitutively active form of TGF-β1 in astrocytes at modest levels develop age-related cerebrovascular abnormalities including thickening of the capillary basement membrane and cerebrovascular amyloid deposition,[22,29] nevertheless, these mice have better cognitive function than nontransgenic controls. Similar microvascular abnormalities are typical for AD and consistent with the observation that TGF-β1 mRNA levels in brains of AD cases correlate positively with vascular amyloid deposition.[22]

TGF-β1 transgenic mice cross-bred with human amyloid precursor (hAPP) transgenic mice, develop synaptic degeneration and amyloid plaques in the brain parenchyma. Unexpectedly, a prominent reduction in plaque formation and overall Aβ accumulation was found in hAPP/TGF-β1 double transgenic compared with hAPP mice.[3] Most of the remaining amyloid accumulated around cerebral blood vessels.

Increased levels of TGF-β1 reduced the number of plaques in human amyloid precursor protein (hAPP) mice by 75% and overall Aβ levels by 60%, compared to mice with normal levels of TGF-β1. Interestingly, TGF-β1 stimulated microglial cells to degrade synthetic Aβ peptide in culture. Because TGF-β1 also caused an activation of microglia in hAPP/TGF-β1 mice, these data suggest that at least some of the effects of TGF-β1 involve the activation of microglial phagocytosis.

The need exists for more effective pharmaceutical compounds for treating and preventing stroke, heart disease, bone loss, cancer, multiple sclerosis, wound healing, inflammation, and neurodegenerative disorders. The present compositions and methods involve small-molecules that modulate TGF-β signaling.

REFERENCES

The following reference and any additional references cited herein are incorporated by reference in their entirety.
1. Lin, A. H., et al. *J. Immunol.* 175, 547-54 (2005).
2. Massa, S. M., et al. *J. Neurosci.* 26, 5288-300 (2006).
3. Wyss-Coray, T., et al. *Nat. Med.* 7, 612-18 (2001).
4. Flanders, K. C., et al. *Prog. Neurobiol.* 54, 71-85 (1998).
5. Buckwalter, M. and Wyss-Coray, T. J. *Neuroinflammation* 1, 10 (2004).

6. Terry, R. D., et al. *Structural basis of the cognitive alterations in Alzheimer disease. in Alzheimer Disease* (eds. Terry, R. D., Katzman, R. & Bick, K. L.) 179-196 (Raven Press, New York, 1994).
7. Brionne, T. C., et al. *Neuron* 40, 1133-45 (2003).
8. Tesseur, I., et al. *J. Clinical Investigation* 116, 3060-69 (2006).
9. Massagué, J., et al. *Cell* 103, 295-309 (2000).
10. Dennler, S., et al. *J. Leukoc. Biol.* 71, 731-40 (2002).
11. Lutz, M. and Knaus, P. *Cell Signal* 14, 977-88 (2002).
12. Letterio, J. J. *Cytokine Growth Factor Rev.* 11, 81-87 (2000).
13. Weinstein, M., et al. *Cytokine Growth Factor Rev.* 11, 49-58 (2000).
14. Yang, Y. C., et al. *Proc. Nat'l. Acad. Sci. USA* 100, 10269-74 (2003).
15. Finch, C. E., et al. *J. Cell. Biochem.* 53, 314-22 (1993).
16. Shi, Y. and Massague, *J. Cell* 113, 685-700 (2003).
17. Luterman, J. D., et al. *Arch. Neurol.* 2000, 1153-60 (2000).
18. Grammas, P. and Ovase, R. *Am. J. Pathol.* 160, 1583-87 (2002).
19. Peress, N. S. and Perillo, E. J. *Neuropathol. Exp. Neurol.* 54, 802-11 (1995).
20. van der Wal, E. A., et al. *Neuroreport.* 4, 69-72 (1993).
21. Tarkowski, E., et al. *Neurobiol. Aging* 23, 237-43 (2002).
22. Wyss-Coray, T., et al. *Nature* 389, 603-06 (1997).
23. Tian, J., et al. *Neurosci. Lett.* 352, 137-40 (2003).
24. Flanders, K. C., et al. *Neurology* 45, 1561-69 (1995).
25. Chao, C. C., et al. *Clin. Diag. Lab. Immunol.* 1, 109-10 (1994).
26. Zetterberg, H., et al. *Neurosci. Lett.* 367, 194-96 (2004).
27. Mocali, A., et al. *Exp. Gerontol* 39, 1555-61 (2004).
28. De Servi, B., et al. *Exp. Gerontol.* 37, 813-21 (2002).
29. Wyss-Coray, T., et al. *Am. J. Pathol.* 156, 139-50 (2000).
30. Oh, S. P., et al., *Proc. Nat'l. Acad. Sci. USA* 97, 2626-31 (2000).
31. Goumans, M. J., et al. *EMBO J.* 21, 1743-53 (2002).
32. Unsicker, K. and Krieglstein, K. *Adv. Exp Med. Biol.* 513, 353-74 (2002).
33. Gross, C. E., et al. *Stroke* 24, 558-62 (1993).
34. Henrich-Noack, P., et al. *J. Stroke* 27, 1609-15 (1996).
35. Pang, L., et al. *Stroke* 32, 544-52 (2001).
36. Boche, D., et al. *J. Cereb. Blood Flow Metab.* 23, 1174-82 (2003).
37. Zhu, Y., et al. *J. Neurosci.* 22, 3898-909 (2002).
38. Prehn, J. H., et al. *Proc. Nat'l. Acad. Sci. USA* 91, 12599-603 (1994).
39. Unsicker, K. and Krieglstein, K. *Cytokine Growth Factor Rev.* 11, 97-102 (2000).
40. Wyss-Coray, T., et al. *Am. J. Pathol.* 147, 53-67 (1995).
41. Luckenbill-Edds, L. *Brain Res. Rev.* 23, 1-27 (1997).
42. Venstrom, K. A. and Reichardt, L. F. *Faseb J.* 7, 996-1003 (1993).
43. Rockenstein, E., et al., *J. Neurosci. Res.* 66, 573-82 (2001).
44. Hutter-Paier, B., et al. *Neuron* 44, 227-38 (2004).
45. Lewis, J., et al. *Nat. Genet.* 25, 402-05 (2000).
46. Greer, L. F., 3rd and Szalay, A. A. *Luminescence.* 17, 43-74 (2002).
47. Contag, C. H. and Bachmann, M. H. *Annu. Rev. Biomed. Eng.* 4, 235-60 (2002).
48. Contag, C. H., et al. *Photochem. Photobiol.* 66, 523-31 (1997).
49. Geusz, M. E., et al. *Curr. Biol.* 7, 758-66 (1997).
50. Barash, I. and Reichenstein, M. *Mol. Reprod. Dev.* 61, 42-48 (2002).
51. Mucke, L., et al. *J. Neurosci.* 20, 4050-58 (2000).
52. Dennler, S., et al. *EMBO J.* 17, 3090-100 (1998).
53. Tesseur, I., et al. *BMC Cell. Biol.* 7, 15 (2006).
54. Luo, J., et al. *Proc. Nat'l. Acad. Sci. USA* 103, 18326-31 (2006).
55. Rothman, S. M. and Olney, J. W. *Trends Neurosci.* 18, 57-58 (1995).
56. Zucchini, S., et al. *Neuroreport.* 13, 2071-74 (2002).
57. Weggen, S., et al. *Nature* 414, 212-16 (2001).
58. Eriksen, J. L., et al. *J. Clin. Invest.* 112, 440-49 (2003).
59. Ertl, P., et al., *J. Med. Chem.* 43, 3714-17 (2000).
60. Clark, D. E. *J. Pharm. Sci.* 88, 815-21 (1999).
61. MacCoss, M. and Baillie, T. A. *Science* 303, 1810-13 (2004).
62. Obach, R. S., et al. *J. Pharmacol. Exp. Ther.* 283, 46-58 (1997).
63. Li, A. P. *Curr Top. Med. Chem.* 4, 701-06 (2004).
64. Jenkins, K. M., et al., *J. Pharm. Biomed. Anal.* 34, 989-1004 (2004).
65. Stoner, C. L., et al. *Int. J. Pharm.* 269, 241-49 (2004).
66. Usansky, H. H. and Sinko, P. J. *J. Pharmacol. Exp. Ther.* 314, 391-99 (2005).
67. Peng, S. X., et al. *Rapid Commun. Mass. Spectrom.* 17, 509-18 (2003).
68. Di, L., et al. *J. Pharm. Sci.* 93, 1537-44 (2004).
69. Dahlgren, K. N., et al. *J. Biol. Chem.* 277, 32046-53 (2002).
70. Ferreira, A., et al. *Mol. Cell. Neurosci.* 9, 220-34 (1997).
71. Hjelmeland, M. D., et al. *Mol. Cancer. Ther.* 3, 737-45 (2004).
72. Callahan, J. F., et al. *J. Med. Chem.* 45, 999-1001 (2002).
73. Uhl, M., et al. *Cancer Res.* 64, 7954-61 (2004).
74. Glaser, K. B., et al. *Mol. Cancer. Ther.* 1, 759-68 (2002).
75. Wang, Q., et al. *Mol. Neurobiol.* 31, 3-16 (2005).
76. Choi, D. W. *J. Neurobiol.* 23, 1261-76 (1992).
77. Schauwecker, P. E. and Steward, O. *Proc. Nat'l. Acad. Sci. USA* 94, 4103-08 (1.997).
78. Terry, R. D., et al. *Ann. Neurol.* 30, 572-80 (1991).
79. Masliah, E., et al. *Ann. Neurol.* 32, 321-29 (1992).
80. Buttini, M., et al. *Neurobiol. Aging* 19 (1998).
81. Palop, J. J., et al. *Proc. Nat'l Acad. Sci. USA* 100, 9572-77 (2003).
82. Wyss-Coray, T., et al. *Proc. Nat'l. Acad. Sci. USA* 99, 10837-42 (2002).
83. Santacruz, K., et al. *Science* 309, 476-81 (2005).
84. Brecht, W. J., et al. *J. Neurosci.* 24, 2527-34 (2004).
85. Harris, F. M., et al. *Proc. Nat'l Acad. Sci. USA* 100, 10966-71 (2003).
86. DeLorey, T. M., et al. *Eur. J. Pharmacol.* 426, 45-54 (2001).
87. DeLorey, T. M., et al. *J. Neurosci.* 18, 8505-14 (1998).
88. Harris, D. L., et al. *Eur. J. Pharmacol.* 401, 271-87 (2000).
89. Fanselow, M. S. *Behav. Brain Res.* 110, 73-81 (2000).

SUMMARY

The present composition and methods are for treating and preventing disorders associated with reduced TGF-β signaling. The following aspects and embodiments thereof described and illustrated below are meant to be exemplary and illustrative, not limiting in scope.

In one aspect, compound having the following structure is provided:

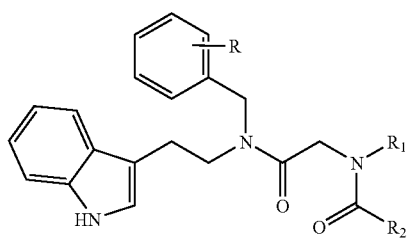

In some embodiments, R is selected from the group consisting of H, halo, alkyl, and substituted alkyl. In particular embodiments, R is selected from the group consisting of H, F, Cl, $CH_3$, $OCH_3$, $N(CH_3)_2$, and $CF_3$.

In some embodiments, $R_1$ is selected from the group consisting of alkyl, allyl, and ether. In particular embodiments, $R_1$ is a cyclic alkyl. In particular embodiments, $R_1$ is $—(CH_2)_n—OCH_3$, wherein n is 1, 2, or 3. In particular embodiments, $R_1$ is $—(CH_2)_nCH_3$, wherein n is 1 or 2. In particular embodiments, $R_1$ is $—(CH_2)_nCH(CH_3)_2$, wherein n is 1 or 2.

In some embodiments, $R_2$ is an aromatic group or a substituted aromatic group. In particular embodiments, $R_2$ is selected from the group consisting of thiophene, methylthiophene, and furan. In particular embodiments, $R_2$ is selected from the group consisting of p-trifluoromethylphenyl and o-chlorophenyl. In some embodiments, $R_2$ is a branched alkyl or cyclic alkyl. In some embodiments, $R_2$ is 2-chloropentane or cyclopropyl.

In some embodiments, the tryptamine of the compound is substituted at one or more of the 4, 5, 6, or 7 positions, and wherein the substitution is independently selected, for each position, from the group consisting of fluoro, methyl, hydroxyl, methoxy, and benzyloxy. In some embodiments, the tryptamine is substituted at one or more of the α or 1 positions, and wherein the substitution is independently selected, for each position, from the group consisting of fluoro, methyl, hydroxyl, methoxy, and benzyloxy.

In particular embodiments, the compound has the structure:

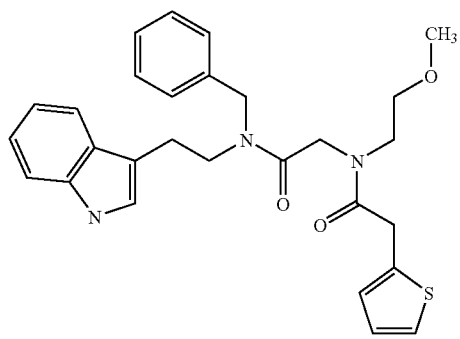

In some embodiments, the compound is a TGF-β agonist.

In another aspect, a compound having the following structure is provided:

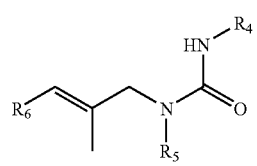

In some embodiments, $R_4$ is selected from the group consisting of thiophene, furan, and cyclic alkyl. In some embodiments, $R_5$ is phenyl or substituted phenyl. In some embodiments, $R_6$ is piperidine or N-substituted piperidine attached via an alkyl group.

In particular embodiments, the compound does not have the structure:

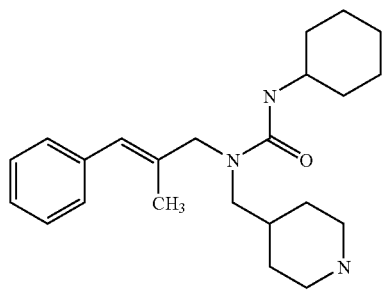

In some embodiments, the compound is a TGF-β agonist.

In another aspect, a compound having the following structure is provided:

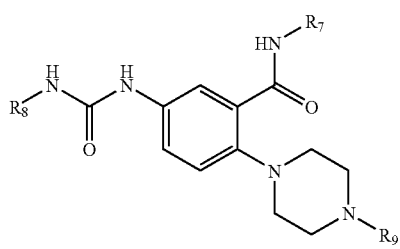

In some embodiments, $R_7$ is selected from the group consisting of H, halo, phenyl, substituted phenyl, and substituted alkyl. In some embodiments, $R_8$ is selected from the group consisting of H, thiophenyl, furanyl, phenyl, substituted phenyl, benzyl, substituted benzyl, and substituted alkyl. In some embodiments, $R_9$ is selected from the group consisting of H, alkyl, alkyne, and substituted alkyl.

In particular embodiments, the compound has the structure:

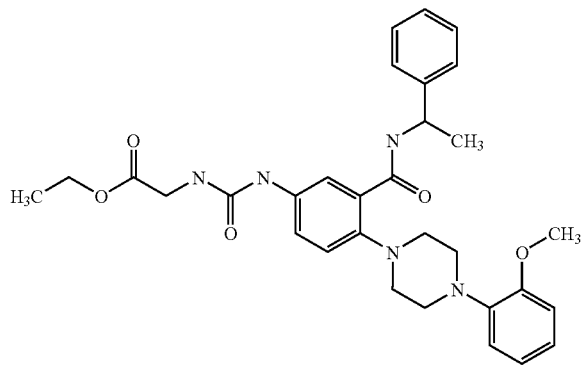

In some embodiments, the compound is a TGF-β agonist.

In another aspect, a pharmaceutical composition comprising one or more of the above compounds is provided. In some embodiments, the pharmaceutical composition is formulated for oral delivery.

In yet a further aspect, a method for increasing TGF-β signaling activity in a mammalian patient is provided, comprising administering one or more of the above compounds.

In particular embodiments, the compound is selected from the group consisting of:

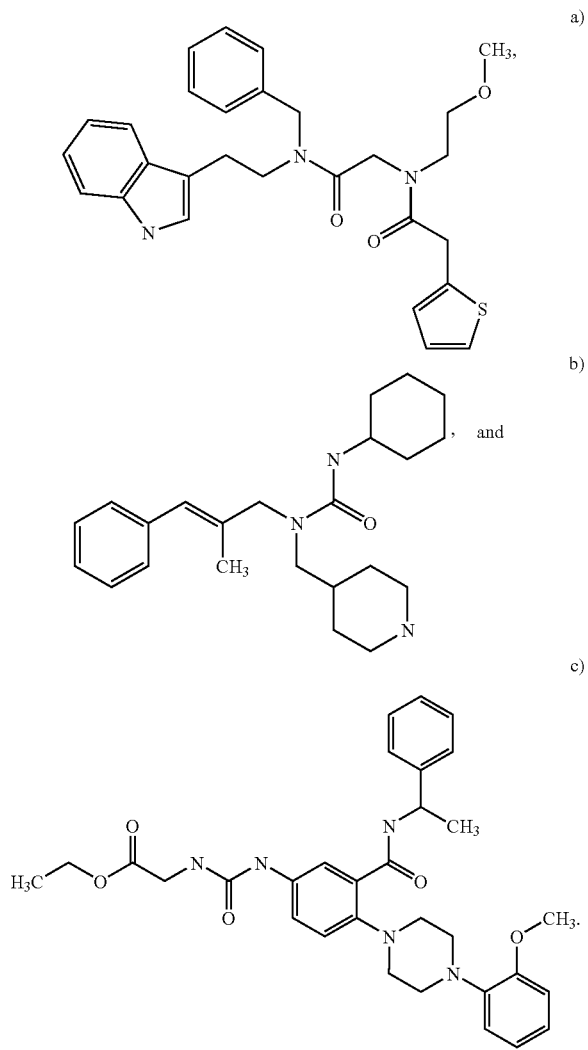

In some embodiments of the method, the increasing TGF-β signaling activity occurs in the brain of the mammalian patient.

In some embodiments, the mammalian patient has a disease or condition characterized by reduced TGF-β signaling activity.

In particular embodiments, the disease or condition is selected from the group consisting of stroke, heart disease, bone loss, cancer, multiple sclerosis, wound healing, inflammation, and a neurological disorder. In particular embodiments, the disease or condition is the disease or condition is Alzheimer's disease (AD).

In some embodiments, the increasing TGF-β signaling activity enhances neuroprotection in the brain. In particular embodiments, the compound reduces the number of amyloid plaques in the brain. In particular embodiments, the compound reduces the accumulation of Aβ in the brain.

In some embodiments, the compound modulates the TGF-β pathway.

In addition to the exemplary aspects and embodiments described above, further aspects and embodiments will become apparent by reference to the drawings and by study of the following descriptions.

BRIEF DESCRIPTION OF THE DRAWINGS

FIGS. 3F and 3G show reporter gene expression in hippocampal neurons of reporter mice following administration of vehicle (F) or an exemplary TGF-β agonist (G).

DETAILED DESCRIPTION

I. Introduction

Figure 1:
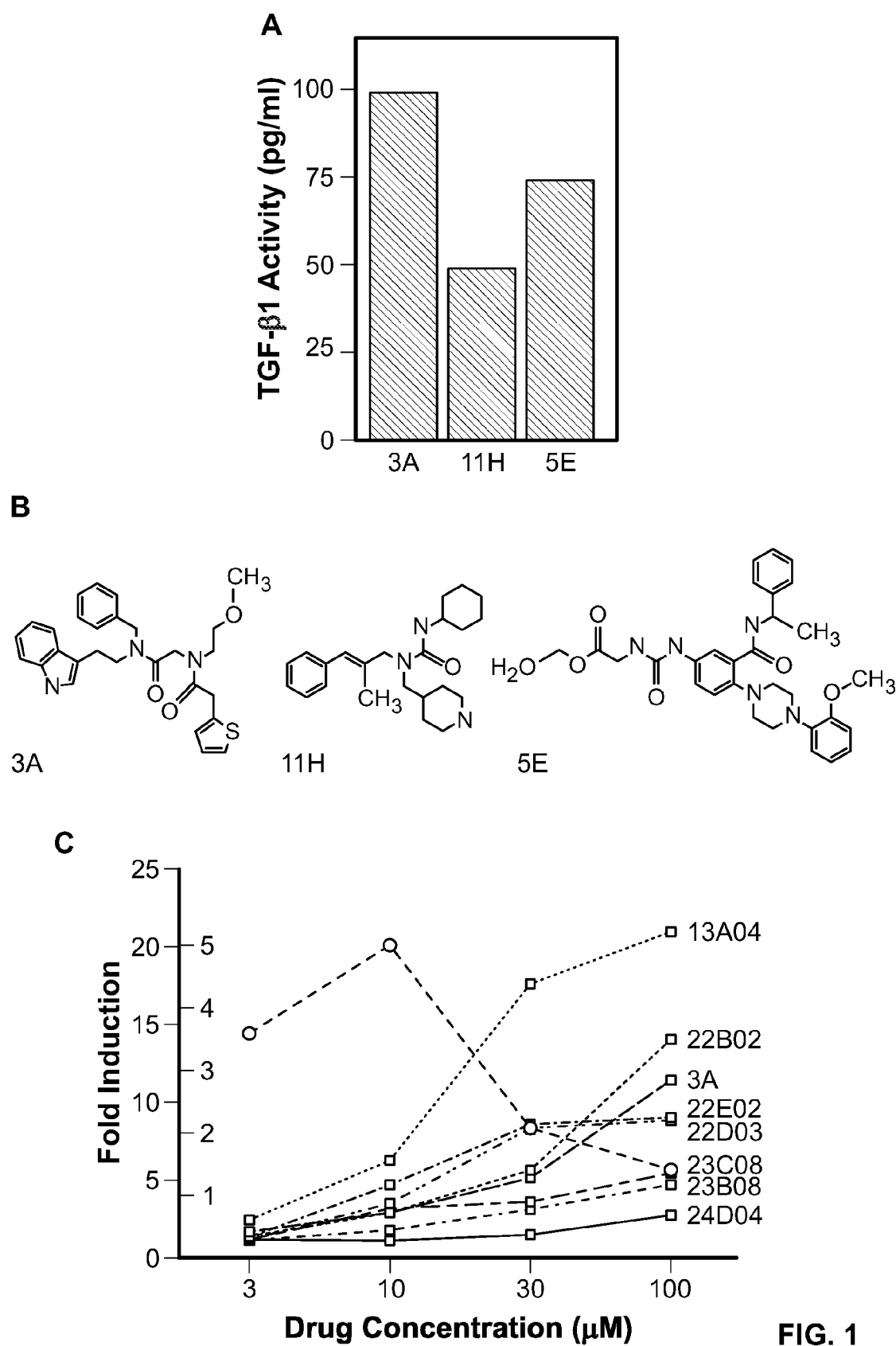
FIGS. 1A-1J relate to small molecule compounds with TGF-β signaling activity and related data. (A) Graph showing relative activity of compounds in reporter cells. (B) Chemical structures. (C) Graph showing fold-induction of TGF-β signaling activity in reporter cells. Structural rendering compounds 3A (D), 11H (G), and 5E (F). (E) Aligned conformations of several agonist compounds. (H) Graph showing neuron survival in cells. (I) Graph showing relative gene expression levels of TGF-β-responsive genes. sulting supernatant was used for luciferase assays. (J) Graph showing luciferase activity in mouse hippocampi resulting from a TGF-β reporter gene.
Figure 1:
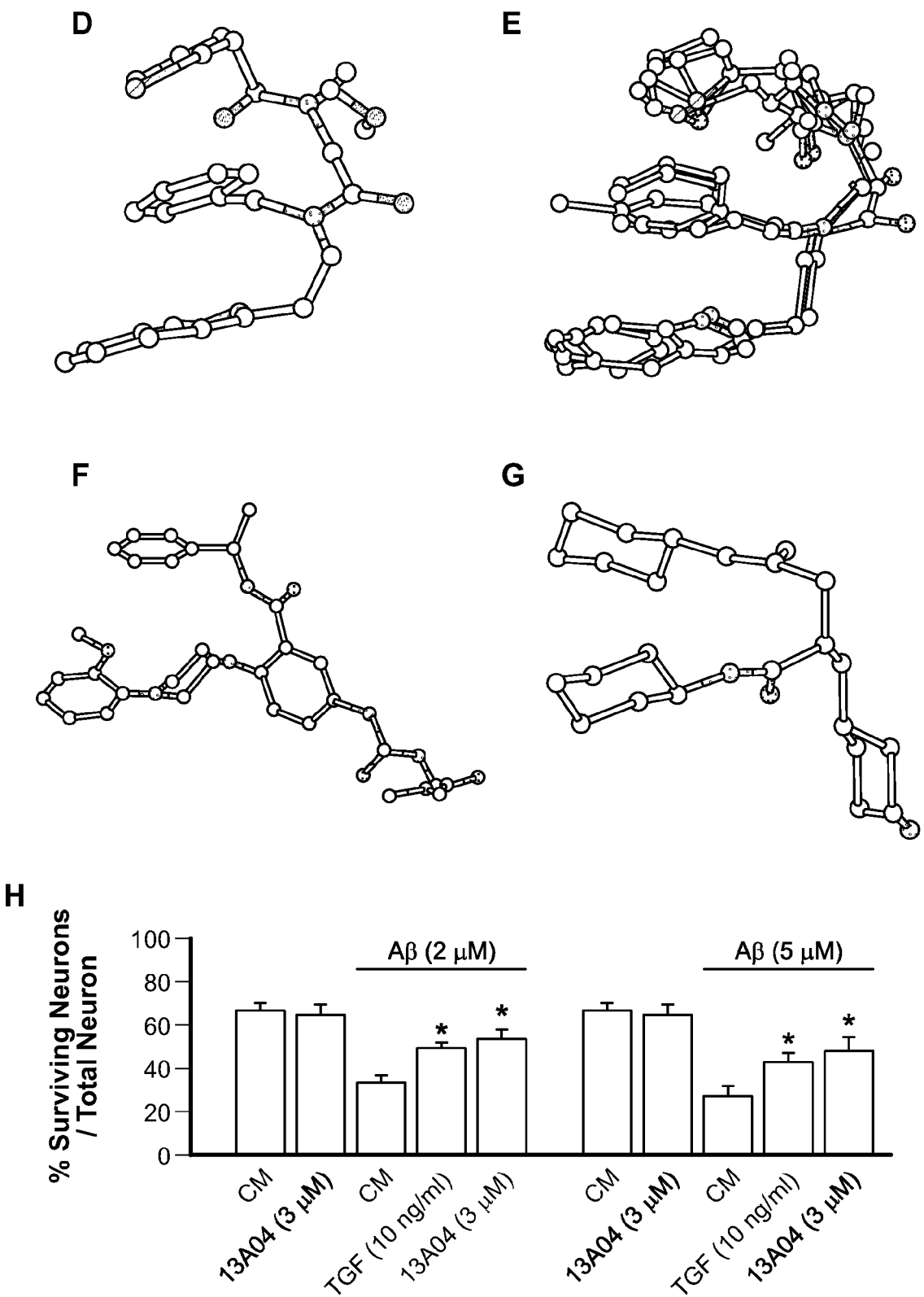
Figure 1:
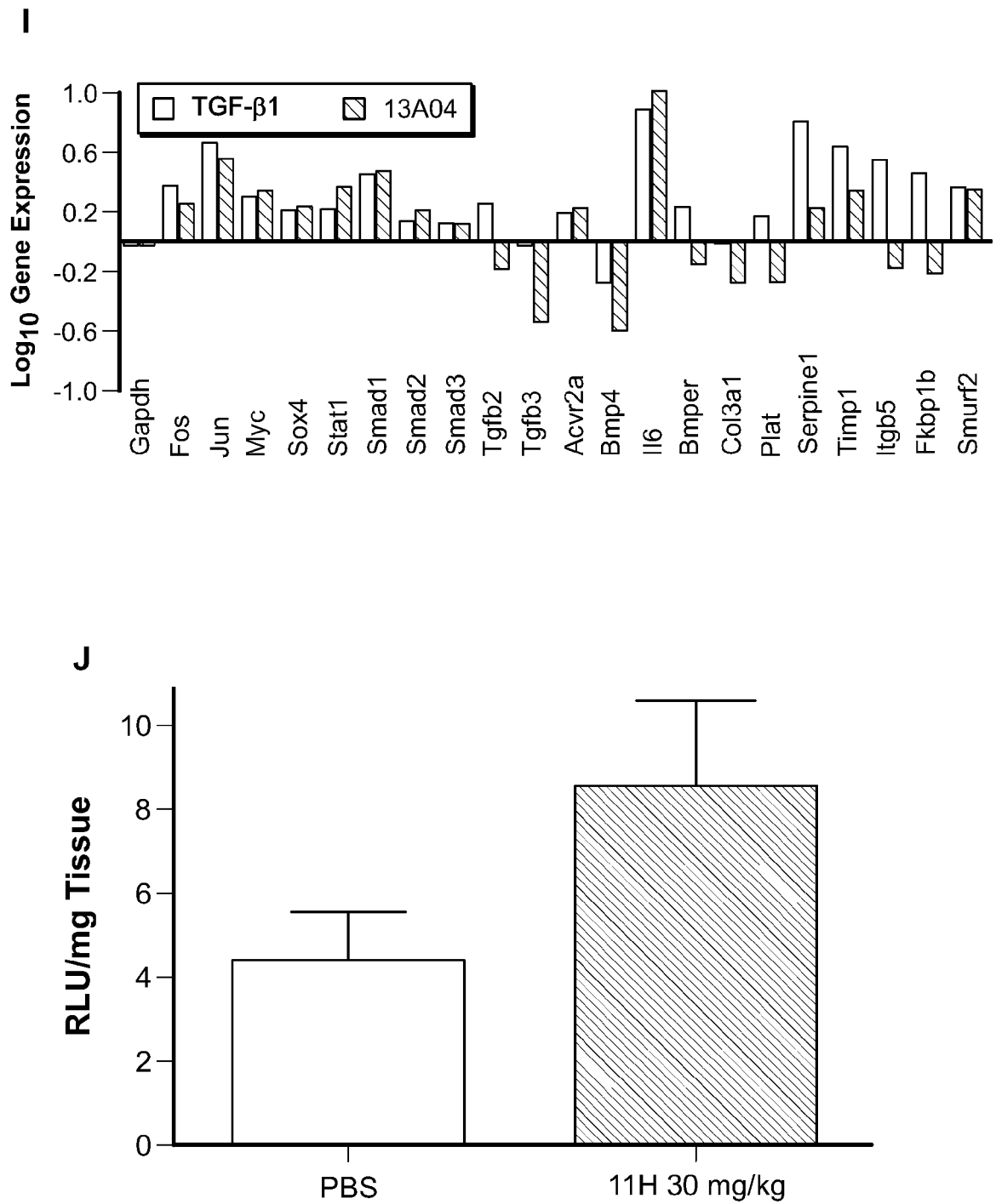

In one aspect, compositions are provided for treating a mammalian patient at risk for or diagnosed with a disease or condition characterized by reduced TGF-β signaling. The compositions are bioactive, small-molecule, TGF-β agonist compounds that cross the blood brain barrier (BBB). Reduction in TGF-β signaling is associated with such diseases and conditions as stroke, heart disease, bone loss, cancer, multiple sclerosis, wound healing, inflammation, and neurodegenerative disorders. TGF-β agonists are known to reduce the number of amyloid plaques and overall accumulation of Aβ in the AD brain.

In another aspect, methods are provided for treating or preventing the progression of a disease or condition characterized by a reduction in TGF-β signaling. On category of such diseases or conditions are neurodegenerative disorders. One example is Alzheimer's disease (AD), or another disease characterized by the deposition of amyloid plaques, and overall accumulation of Aβ in the brain. Examples of such diseases are described, infra.

Experiments performed in support of the present compositions and methods are described, below.

II. TGF-β Reporter Gene and Cells for Screening Compounds

An in vitro screening method was developed to identify small-molecule chemical compounds with TGF-β1-like bioactivity. The method utilized a fusion gene consisting of the luciferase or secreted alkaline phosphatase (SEAP) reporter gene under control of the TGF-β responsive Smad-binding element (SBE) minimal promoter sequence.[52] To screen for compounds that mimic TGF-β bioactivity, reporter cell lines were prepared by stably-integrating SBE-SEAP into C6 astrocytoma cells, a primary astrocyte line derived from tgfb1$^{-/-}$ mice, a mouse embryonic fibroblast cell line derived from tgfb1$^{-/-}$ mice (MFB-F11), and NG108-15 neuroblastoma cells (Table 1). Such cell lines remained stable for at least 20 passages.[53] Use of a tgfb1$^{-/-}$ genetic background avoids interference by the exogenous tgfb1 gene.

TABLE 1

Cell lines for screening of compounds with TGF-β signaling activity

| Cell line | Origin | Reporter gene | Colonies/ lines tested | Lines selected | Average fold induction** |
|---|---|---|---|---|---|
| C6 | Rat astrocytoma | SBE-SEAP* | 34 | 6 | 7 (line 29) |
| MFB | Mouse fibroblast, Tgfb1$^{-/-}$ | SBE-SEAP | 49 | 7 | >500 (line F11) |
| MAB39 | Mouse primary astrocytes, Tgfb1$^{-/-}$ | SBE-SEAP | 54 | 2 | 3 (line 66) |
| NG108-15 | Mouse neuroblastoma | SBE-SEAP | 46 | 5 | 18 (line H18) |

*using 1 ng/ml TGF-β1, # SBE, Smad binding element; SEAP, secreted alkaline phosphatase
**best cell line *

III. Initial Compound Screening

A library with 5,000 chemically diverse small molecules (average Mr 200 Da) was obtained from Comgenex LLC (South San Francisco, Calif.). To test compounds, or to assay individual stably transfected cell lines for responsiveness to TGF-β1, 4×10$^4$ cells were seeded in 10% FBS/DMEM into 96-well plates and incubated overnight, washed twice, and exposed to test compounds (at 4 or 20 μM) or recombinant TGF-β1 (at 0 to 1,000 pg/ml) in serum free medium (DMEM). Conditioned medium was assayed for SEAP activity 24 and 48 hours later.

All compounds were tested twice, in duplicate, using the MFB-F11 cell line. 80 compounds were selected for further study based on induction of the reporter gene in any of the replicates. These compounds were tested again in MFB-F11 or C6-H4 cells, either alone or in the presence of 100 pg/ml of TGF-β1, to test for synergistic activities. Several compounds showed activities of up to an equivalent of 100 pg/ml TGF-β1 at 20 μM in the TGF-β1 deficient MFB-F11 cells. Some compounds showed dose-dependent activities. The most promising compounds (i.e., the three most active "hits") were 3A, 11H, and 5E, having the propose IUPAC names N-(2-(1H-indol-3-yl)ethyl)-N-benzyl-2-(N-(2-methoxyethyl)-2-(thiophen-2-yl)acetamido)acetamide, (E)-3-cyclohexyl-1-(2-methyl-3-phenylallyl)-1-(piperidin-4-ylmethyl)urea, and ethyl 2-(3-(4-(4-(2-methoxyphenyl)piperazin-1-yl)-3-(1-phenylethylcarbamoyl)phenyl)ureido)acetate, respectively, and the following structures:

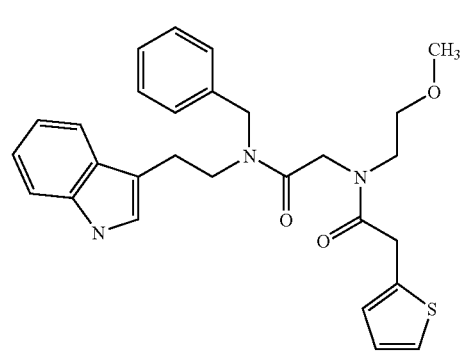

3A

-continued

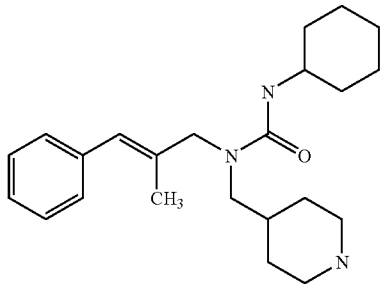

11H

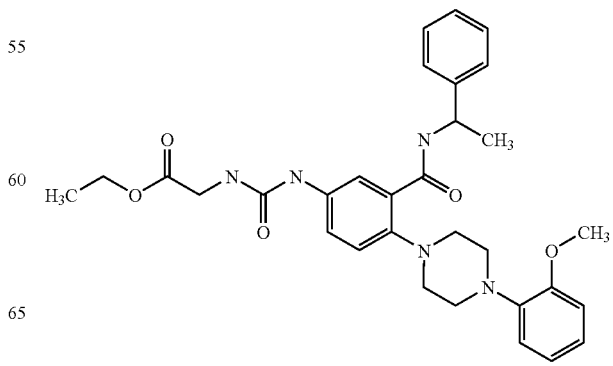

5E

Data relating to these three lead compounds are shown in FIGS. 1A-1J. FIG. 1A is a graph showing the relative activity of compounds 3A, 11H, and 5E following independent addition to MFB-F11 reporter cells at 20 µM (3A, 5E) or 10 µM (11H). SEAP activity was compared to a standard curve generated with cells exposed to different concentrations of recombinant TGF-β1. The chemical structures of 3A, 11H, and 5E are, shown in FIG. 1B. FIG. 1C is a graph showing fold-induction of TGF-β signaling activity in MFB-F11 reporter cells by compound 3A and 7 analogs (scale 0 to 25 fold) and compound 11H (circles, stippled line; scale 0 to 5). FIGS. 1D, 1F, and 1G show structural renderings of compounds 3A, 11H, and 5E, respectively.

FIG. 1H is a graph showing the relative amount of surviving 6-7 DIV hippocampal neurons of E16 mice following exposure to culture medium (CM) alone, 13A04 (3 µM), or CM containing Aβ at 2 or 5 µM with TGF-β1 (10 ng/ml) or 13A04 (3 µM). After 24 hours, cultures were fixed and surviving cells were counted. Data represent mean±SEM, n=3-7 fields counted per plate. All conditions were compared to Aβ using the Mann-Whitney test (* $p<0.05$, ** $p<0.01$). FIG. 1I is a graph showing the relative gene expression levels of the indicated TGF-β-responsive genes induced in MFB-F11 fibroblasts stimulated with TGF-β1 (yellow) or 13A04 (blue) for 24 h. mRNA was extracted, labeled and hybridized to gene expression arrays tailored for the TGF-β pathway. FIG. 1J shows activation of a TGF-β reporter gene in the hippocampi of mice injected with 11H. These data demonstrate that compounds 3A, 11H, and 5E are TGF-β-agonists.

Compounds 3A and 5E were not found in a searchable drug database. Compound 11H is distributed by Comgenex (the provider of the library).

IV. Second Compound Screening

Compounds 3A, 5E, and 11H from the initial screening were analyzed using the GASP pharmacophore modeling program, which is part of the Sybyl molecular modeling software (Tripos, Inc). GASP allows mapping the important functional elements into three-dimensional space without prior knowledge of geometric constraints or receptor structure. The building of a three-dimensional pharmacophore model allows the rational design of small-molecule inhibitors with modified flexibility constraints and/or hydrophobic and electrostatic properties.

A. Compounds Based on the 3A Core

The energy-minimized structure of compound 3A revealed a unique conformation as shown in FIG. 1D. The three most active compounds (i.e., 13A04, 22B02, and 3A) assume similar conformations when docked (FIG. 1E). Several analogs of 3A were able to activate the TGF-β reporter in MFB-F11 cells, some of them with higher potency than the original compound (FIG. 1C and Tables 2A and 2B). Induction of the TGF-β reporter gene ranged from 20.9 fold to no induction.

Tables 2A and 2B shows the structures and biological properties, respectively, of the additional compounds/hits related to compound 3A (highlighted in grey). 3A-based compounds are based on the following core structure:

TABLE 2A

Structure activity of lead compounds related to 3A.

| Compound | R | $R_1$ | $R_2$ |
|---|---|---|---|
| 13A04 | —H | —$CH_2CH(CH_3)_2$ | furan |
| 22B02 | —$CH_3$ (p) | —$(CH_2)_2$—$OCH_3$ | cyclopropyl |
| 3A | —H | —$(CH_2)_2$—$OCH_3$ | thiophene |
| 22E02 | —F (p) | —$(CH_2)_3$—$OCH_3$ | phenyl-$CF_3$ |
| 21B08 | —$CF_3$ (p) | —$(CH_2)_3$—$OCH_3$ | thiophene |
| 13F03 | —F (p) | —$(CH_2)_2$—$OCH_3$ | isopropyl-Cl |
| 22D03 | —F (p) | —$(CH_2)_3$—$OCH_3$ | chlorophenyl |
| 21F11 | —$CF_3$ (p) | —$CH(CH_3)_2$ | dimethyl-nitrophenyl |
| 23C08 | —$N(CH_3)_2$ (p) | —$CH_2CH(CH_3)_2$ | fluorophenyl |

TABLE 2A-continued

Structure activity of lead compounds related to 3A.

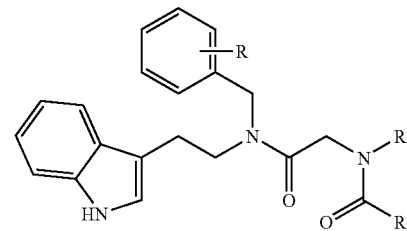

3A core

| Compound | R | R₁ | R₂ |
|---|---|---|---|
| 37B02 | —OCH₃ (o) | —(CH₂)₂—OCH₃ | 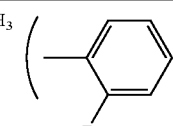 |
| 23D05 | —N(CH₃)₂ (p) | —CH(CH₃)₂ | 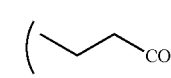 |
| 23B08 | —N(CH₃)₂ (p) | —CH(CH₃)₂ | 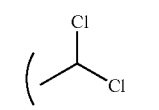 |
| 23A08 | —N(CH₃)₂ (p) | —CH(CH₃)₂ | 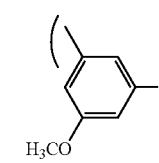 |
| 37C02 | -3,4-Cl | —CH(CH₃)₂ | 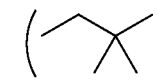 |
| 21A11 | —CF₃ (p) |  | 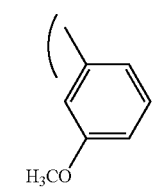 |
| 44A04 | —H |  |  |
| 21C09 | —CF₃ (p) | —(CH₂)₂—OCH₃ | 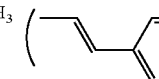 |
| 22B05 | —F (p) | —(CH₂)₂—OCH₃ | 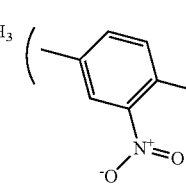 |

TABLE 2A-continued

Structure activity of lead compounds related to 3A.

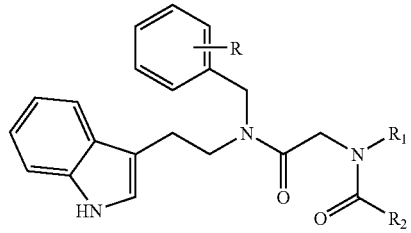

3A core

| Compound | R | R₁ | R₂ |
|---|---|---|---|
| 13G03 | —OCH₃ (o) |  |  |
| 21A08 | —CF₃ (p) | —(CH₂)₃—OCH₃ | 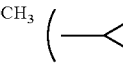 |
| 24D04 | -3,4-OCH₃ | —(CH₂)₂—OCH₃ |  |

Relative TGF-β activity in the cell reporter assay at four different concentrations and calculated log P, tPSA (topological polar surface area; a measure of passive molecular transport through membranes,[59] and log BB (a measure of blood-brain barrier penetration[60]) are shown in Table 2B. A tPSA of <60 and C log P of from about 1.5 to about 2.5 are preferred.

TABLE 2B

Structure activity of lead compounds related to 3A.

| | Relative TGF-β activity* | | | | | | |
|---|---|---|---|---|---|---|---|
| | 100 μM | 30 μM | 10 μM | 3 μM | CLogP | tPSA | Log BB |
| 13A04 | 20.9 | 17.6 | 6.3 | 2.5 | 4.85 | 76.9 | −0.26 |
| 22B02 | 14.1 | 5.7 | 2.9 | 1.4 | 4.34 | 76.9 | −0.34 |
| 3A | 11.4 | 5.2 | 2.9 | 1.7 | 4.46 | 76.9 | −0.32 |
| 22E02 | 9.1 | 8.6 | 4.7 | 1.4 | 6.09 | 76.9 | −0.07 |
| 21B08 | 9.1 | 7.0 | 4.8 | 1.6 | 5.59 | 76.9 | −0.15 |
| 13F03 | 9.1 | 3.8 | 1.9 | 1.3 | 4.77 | 76.9 | −0.27 |
| 22D03 | 8.8 | 8.3 | 3.7 | 1.4 | 5.86 | 76.9 | −0.11 |
| 21F11 | 6.5 | 2.7 | 1.6 | 0.8 | 5.40 | 110.1 | −0.67 |
| 23C08 | 5.4 | 3.6 | 3.1 | 1.3 | 6.06 | 65.5 | 0.09 |
| 37B02 | 5.2 | 4.7 | 1.9 | 1.1 | 4.82 | 91.0 | −0.48 |
| 23D05 | 4.7 | 1.7 | 1.1 | 0.8 | 5.15 | 101.9 | −0.59 |
| 23B08 | 4.5 | 3.1 | 1.8 | 1.1 | 5.25 | 65.5 | −0.03 |
| 23A08 | 3.4 | 2.8 | 2.3 | 1.2 | 5.47 | 93.7 | −0.42 |
| 37C02 | 3.1 | 1.4 | 1.0 | 0.7 | 6.93 | 62.8 | 0.26 |
| 21A11 | 2.9 | 2.3 | 2.3 | 1.3 | 5.67 | 76.9 | −0.14 |
| 44A04 | 2.8 | 2.7 | 2.3 | 1.2 | 4.58 | 62.8 | −0.09 |
| 21C09 | 2.8 | 1.9 | 1.7 | 1.0 | 6.46 | 76.9 | −0.02 |
| 22B05 | 2.8 | 1.7 | 1.2 | 1.1 | 5.32 | 124.2 | −0.89 |
| 13G03 | 2.7 | 2.6 | 2.5 | 1.5 | 4.27 | 76.9 | −0.35 |
| 21A08 | 2.7 | 1.9 | 1.5 | 1.1 | 6.59 | 76.9 | 0.00 |
| 24D04 | 2.7 | 1.5 | 1.1 | 1.2 | 4.47 | 105.1 | −0.74 |

*Fold change compared with vehicle

Figure 5:
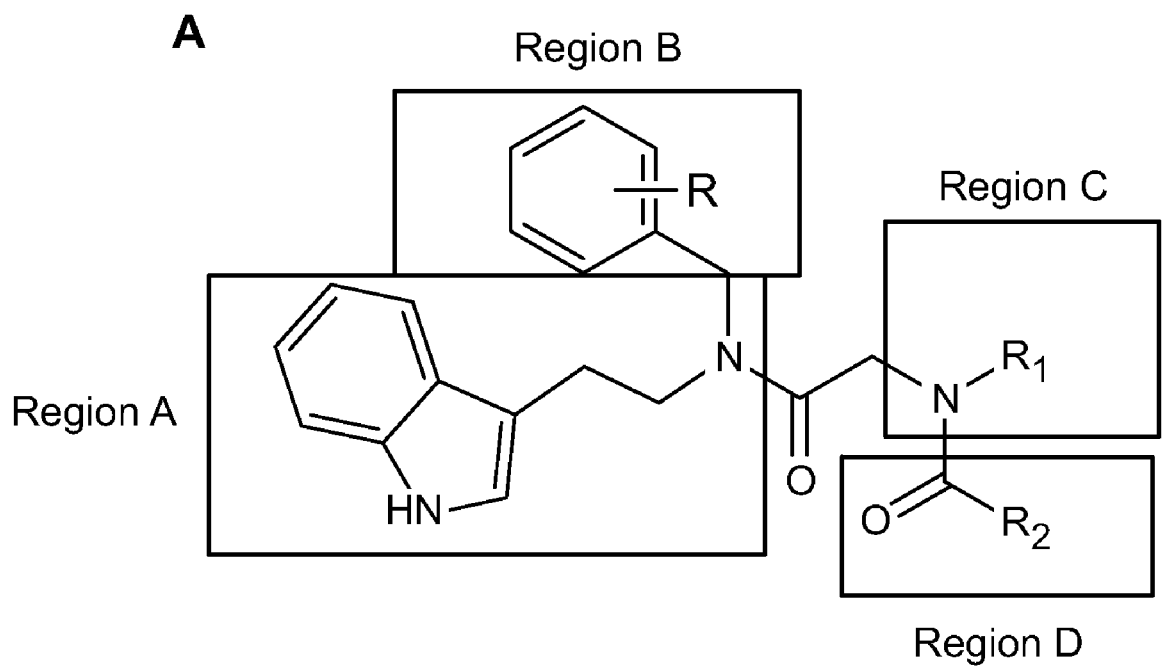
FIG. 5A illustrates regions of the 3A compound.
FIG. 5B shows a 3-D space filling model of 3A.
Figure 5:
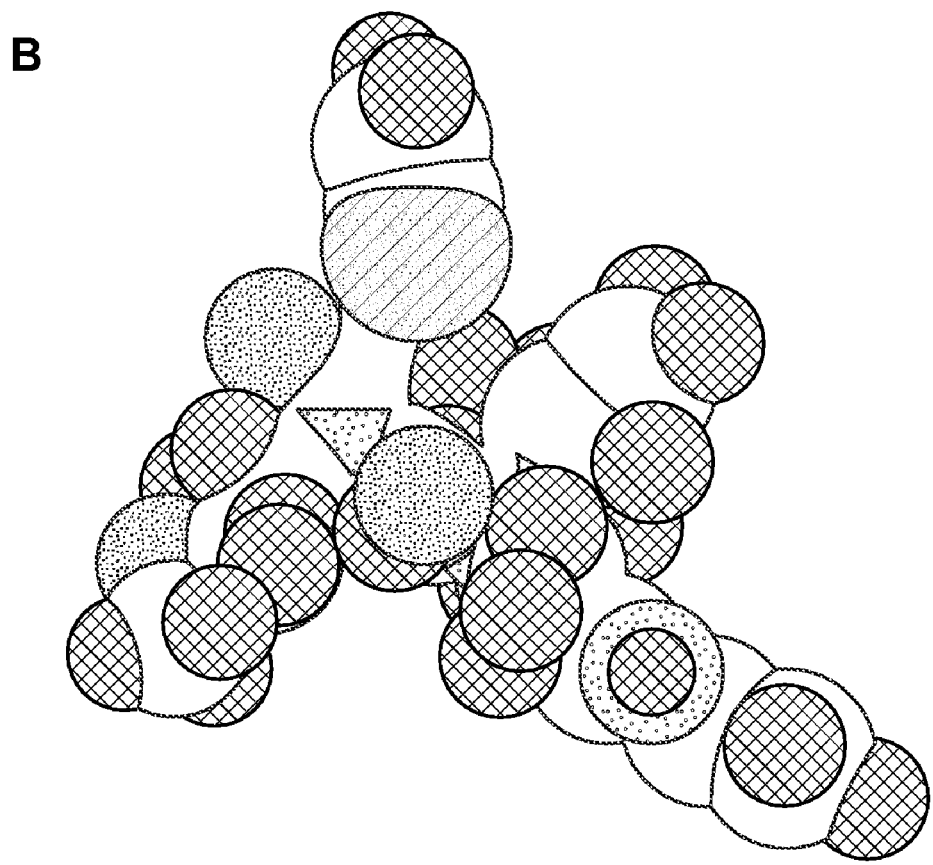

Docking of several of the most active compounds, as exemplified, in FIG. 1E, suggested that the 3A-related compounds included four regions that can be modified to tailor the compound a particular application. For example, structural features that enhance activity and oral bioavailability can be combined in the same compound. The four regions are shown in FIG. 5A. A three-dimensional, space-filling model of alignments is shown in FIG. 5B.

The tryptamine in Region A remained unchanged within the tested series of compounds; however, a 5-fluoro-, 5-chloro-, 5-methyl-, 5-hydroxy-, 5-methoxy-, 5-benzyloxy, or similar substitutions at one or more of the 4, 6, or 7 positions of the ring structure are contemplated. α-methyl and 1-methyl tryptamine substitutions are also contemplated. Other structural modifications that are expected to produce compounds with suitable activity and pharmacokinetic properties (i.e., based on the results shown in Tables 2A and 2B) are shown in Table 3, where R, $R_1$, and $R_2$ are as indicated in the above 3A core structure and in FIG. 5A.

From the screening data it appears that region B should be aromatic, with limited substitution, which may include basic groups such as dimethyl amine. Activity is lost, when R has a bulky substitution and $R_2$ is also bulky; therefore, small heterocyclic rings or minimally substituted aromatic rings are proposed for region B. Region C and $R_1$ should be small and lipophilic or a straight chain alcohol. The addition of a ring system connecting regions A and B is also contemplated, and expected to reduce flexibility, constrain the three-dimensional configuration, and possibly increase activity. In one example, the A and B regions are linked using a backbone harboring a β-carboline to which additional R groups can be added.

Figure 7A:
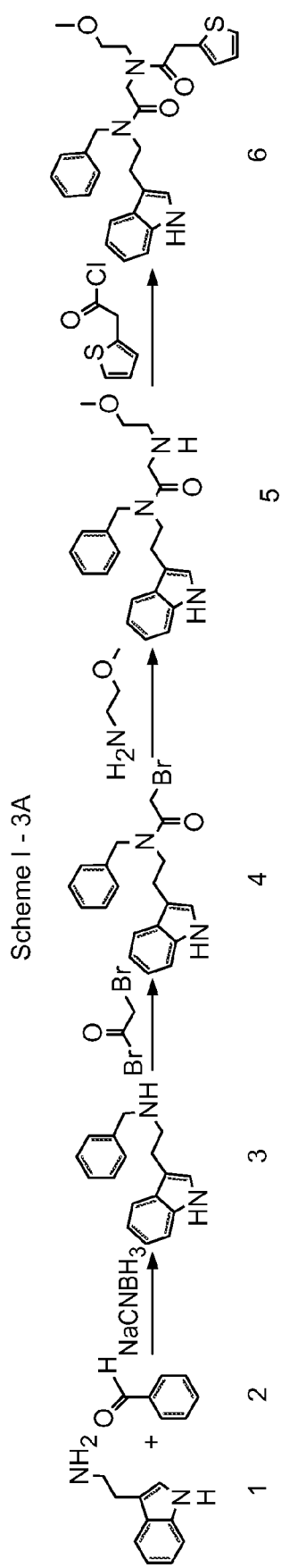
FIGS. 7A and 7B illustrate synthesis schemes for compounds 3A and 11H, respectively.

An exemplary process of making the 3A compound is shown as Scheme I in FIG. 7A. Intermediate compounds 3-5 also expected to possess suitable activity and pharmacokinetic properties.

TABLE 3

Exemplary R groups for attachment to the 3A core.

| R | $R_1$ | $R_2$ | | |
|---|---|---|---|---|
| —H | —$CH_2CH(CH_3)_2$ | 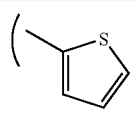 or 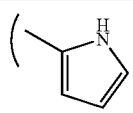 | | |
| —$CF_3$ | —$CH_2CH(CH_3)_2$ | 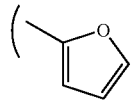 or 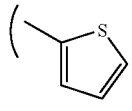 or 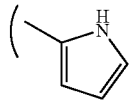 | | |
| —H | —$CH_2N(CH_3)_2$ | 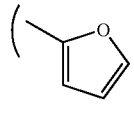 or 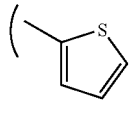 or 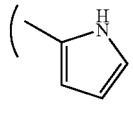 | | |
| —$CF_3$ | —$(CH_2)_3$—$OCH_3$ | 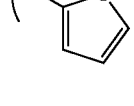 or 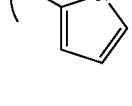 or 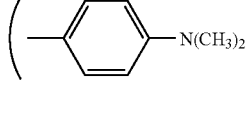 | | |
| —F | —$(CH_2)_3$—$OCH_3$ | 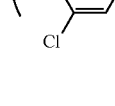 or 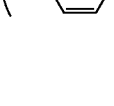 or 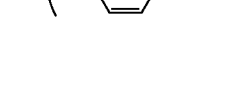 | | |
| —$N(CH_3)_2$ | —$(CH_2)_2$—$OCH_3$ | 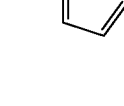 or 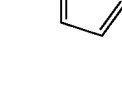 or  | | |
| —H | —$(CH_2)_2$—$OCH_3$ |  or  or 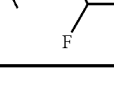 | | |

B. Compounds Based on the 11H Core

Figure 6:
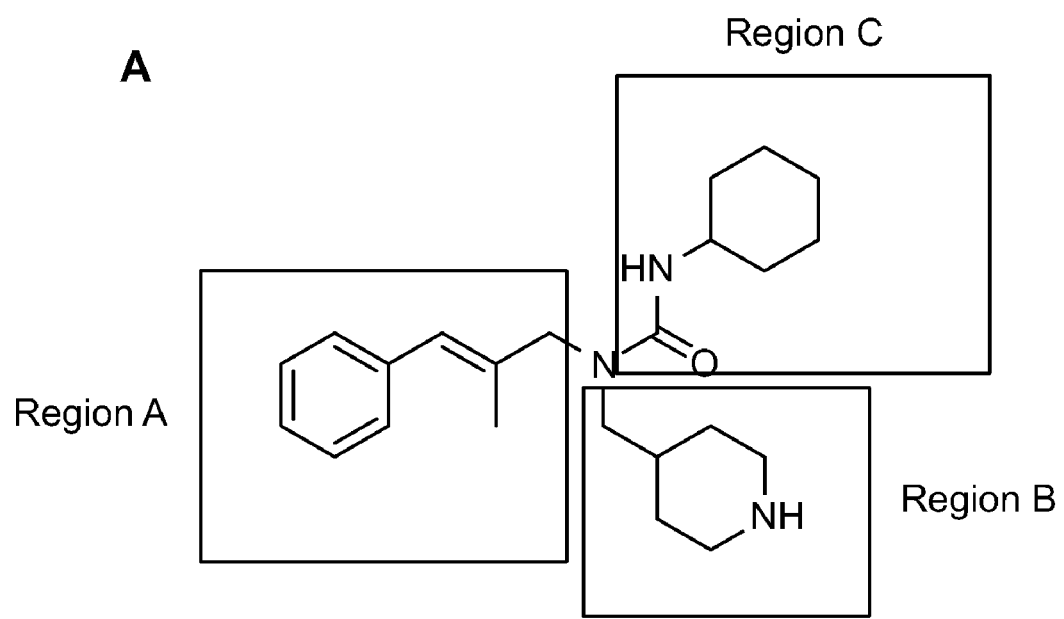
FIG. 6A illustrate regions of the 11H compound.
FIG. 6B shows a 3-D space filling model of 11H.
Figure 6:
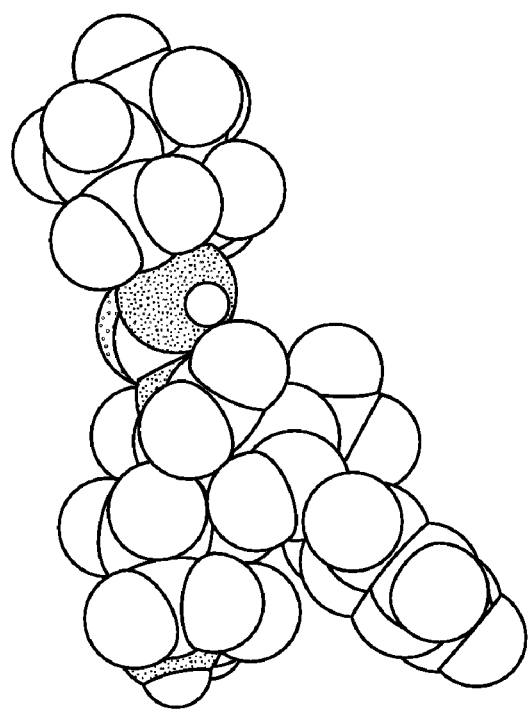

FIG. 6A shows three regions of the 11H-based compounds that can be modified to tailor the compound a particular application (based on alignments and structure-activity analyses, as discussed above). A three-dimensional, space-filling model is shown in FIG. 6B. Based on the core structure shown below, the R groups exemplified in Table 4 are expected to produce active compounds.

TABLE 4

Compounds based on the 11H core.

11H core

| Compound | $R_4$ | $R_5$ | $R_6$ |
|---|---|---|---|
| CGX-0540523 | 2-thienyl | phenyl | 4-piperidinylmethyl with N-C(=O)-O-(4-chlorophenyl) |
| CGX-0540547 | 2-thienyl | phenyl | 4-piperidinylmethyl with N-C(=O)-cyclobutyl |
| CGX-0540672 | 2-furyl | phenyl | 4-piperidinylmethyl with N-C(=O)-2-naphthyl |
| CGX-0541586 | cyclopropyl | phenyl | 4-piperidinylmethyl with N-C(=O)-phenyl |

Figure 7B:
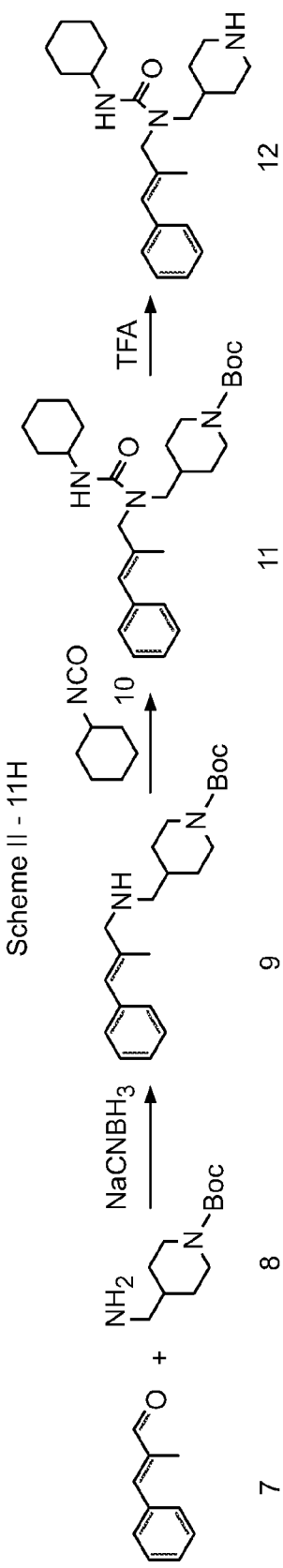

An exemplary scheme for synthesizing a second series of compounds related to compound/hit 11H is shown as Scheme II in FIG. 7B. Intermediates in the synthesis are expected to have activity similar to that of 11H.

C. Compounds Based on the 5E Core

Several 5E-related compounds have also been synthesized for testing in the described assays. Table 5 identifies R groups expected to produce an active compound, based on the following core structure:

TABLE 5
Compounds based on the 5E core
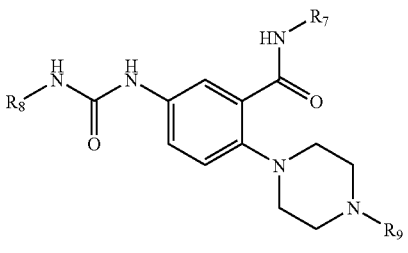
5E core
| Name | R7 | R8 | R9 |
|---|---|---|---|
| CGX-0730795 | —CH(CH$_3$)$_2$ | 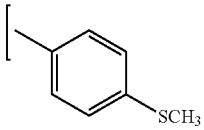 | 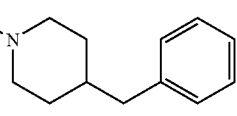 |
| CGX-0731125 | —(CH$_2$)$_5$ | 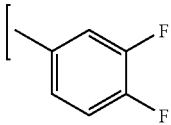 | —N(CH$_3$)$_2$ |
| CGX-00731278 | 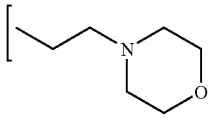 | 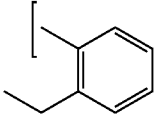 | 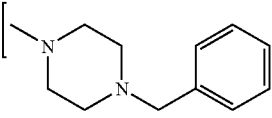 |
| CGX-0731359 | 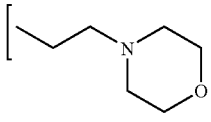 | 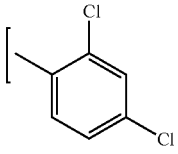 | 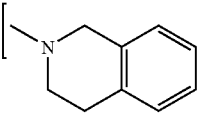 |
| CGX-0731462 | 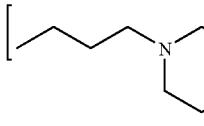 | 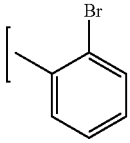 | 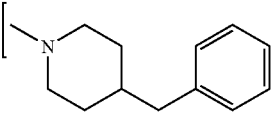 |
| CGX-0733464 | —CH$_2$CH(CH$_3$)$_2$ | 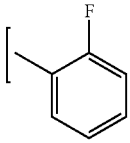 | 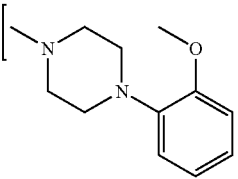 |
| CGX-0733818 | —(CH$_2$)$_5$ | 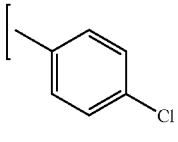 | 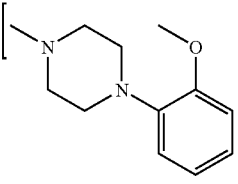 |

TABLE 5-continued
Compounds based on the 5E core
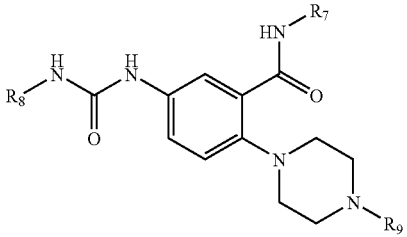
5E core
| Name | R7 | R8 | R9 |
|---|---|---|---|
| CGX-0733942 | 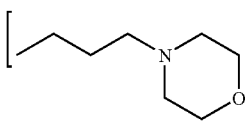 |  | 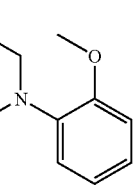 |
| CGX-0740410 | —CH$_2$CH$_2$CH(CH$_2$CH$_3$)$_2$ | 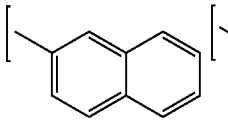 | 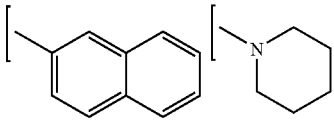 |
| CGX-0740492 | 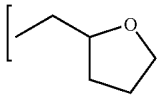 | 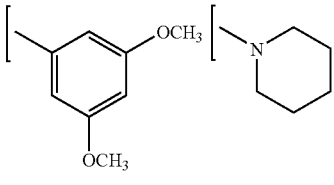 | 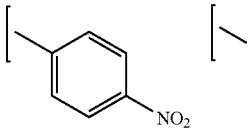 |
| CGX-0740613 | —CHCH$_3$(CH$_2$CH$_3$) | 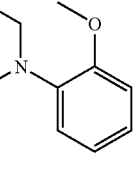 | 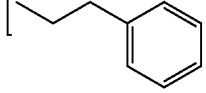 |
| CGX-0740807 | 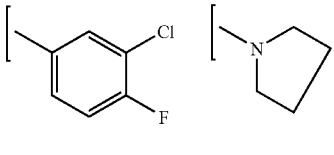 | 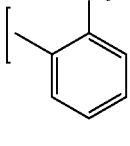 |  |
| CGX-0740885 | —CH$_2$CH$_2$CH$_3$ | 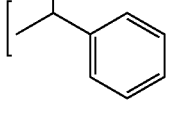 | 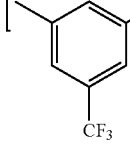 |
| CGX-0741048 | 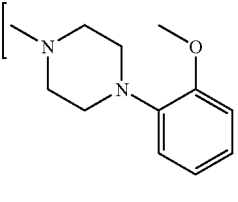 | | |

TABLE 5-continued

Compounds based on the 5E core

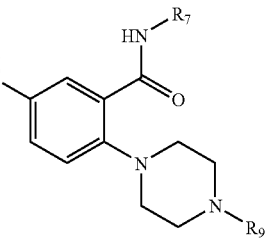

5E core

| Name | R<sub>7</sub> | R<sub>8</sub> | R<sub>9</sub> |
|---|---|---|---|
| CGX-0730795 | —CH(CH$_3$)$_2$ | 4-(SCH$_3$)-phenyl | 4-benzylpiperidinyl |
| CGX-0731125 | —(CH$_2$)$_5$ | 3,4-difluorophenyl | —N(CH$_3$)$_2$ |
| CGX-00731278 | propyl-morpholinyl | 2-ethylphenyl | 4-benzylpiperazinyl |
| CGX-0731359 | propyl-morpholinyl | 2,4-dichlorophenyl | tetrahydroisoquinolinyl |
| CGX-0731462 | butyl-morpholinyl | 2-bromophenyl | 4-benzylpiperidinyl |
| CGX-0733464 | —CH$_2$CH(CH$_3$)$_2$ | 2-fluorophenyl | 4-(2-methoxyphenyl)piperazinyl |
| CGX-0733818 | —(CH$_2$)$_5$ | 4-chlorophenyl | 4-(2-methoxyphenyl)piperazinyl |

TABLE 5-continued

Compounds based on the 5E core

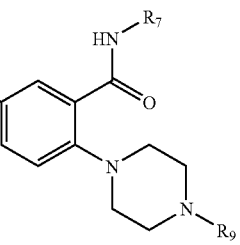

5E core

| Name | R₇ | R₈ | R₉ |
|---|---|---|---|
| CGX-0741060 | isopropylphenyl | —CH₂CO₂CH₂CH₃ | piperazinyl-(2-methoxyphenyl) |
| CGX-0741107 | isopropylphenyl | 3,5-difluorophenyl | 4-methylpiperidinyl |
| CGX-0741157 | cyclopropyl | 2-bromophenyl | pyrrolidinyl |
| CGX-0741186 | cyclopropyl | 2-ethoxyphenyl | pyrrolidinyl |
| CGX-0741210 | —(CH₂)₂OCH₃ | 3-bromophenyl | pyrrolidinyl |
| CGX-0741328 | 4-fluorobenzyl | —CH₂CO₂CH₂CH₃ | pyrrolidinyl |
| CGX-0746144 | —(CH₂)₂CHCH₃(CH₂)₂— | 4-(CO₂Et)phenyl | piperidinyl |
| CGX-0730795 | —CH(CH₃)₂ | 4-(SCH₃)phenyl | 4-benzylpiperidinyl |

TABLE 5-continued

Compounds based on the 5E core 5E core

| Name | R7 | R8 | R9 |
|---|---|---|---|
| CGX-0731125 | —(CH2)5 | 3,4-difluorophenyl | —N(CH3)2 |
| CGX-00731278 | propyl-morpholine | 2-ethylphenyl | N-benzylpiperazine |
| CGX-0731359 | propyl-morpholine | 2,4-dichlorophenyl | tetrahydroisoquinoline |
| CGX-0731462 | butyl-morpholine | 2-bromophenyl | 4-benzylpiperidine |
| CGX-0733464 | —CH2CH(CH3)2 | 2-fluorophenyl | N-(2-methoxyphenyl)piperazine |
| CGX-0733818 | —(CH2)5 | 4-chlorophenyl | N-(2-methoxyphenyl)piperazine |
| CGX-0746262 | —(CH2)3OCH3 | 2,6-diisopropylphenyl | piperidine |

TABLE 5-continued

Compounds based on the 5E core 5E core

| Name | R₇ | R₈ | R₉ |
|---|---|---|---|
| CGX-0746351 | —(CH₂CH₃)₂ | 4-nitrophenyl | pyrrolidin-1-yl |
| CGX-0746781 | cyclopropyl | adamantyl | 4-(2-methoxyphenyl)piperazin-1-yl |
| CGX-0746908 | cyclopropyl | 2,4-dimethylphenyl | 4-methylpiperidin-1-yl |
| CGX-0747015 | —(CH₂)₂OCH₃ | 3-chloro-4-methylphenyl (2-methyl) | 4-methylpiperidin-1-yl |
| CGX-0747197 | tetrahydrofuran-2-ylmethyl | 2-fluorophenyl | 4-benzylpiperidin-1-yl |
| CGX-0747389 | —(CH₂)₃OCH₃ | 2,6-dichlorophenyl | 4-benzylpiperidin-1-yl |
| CGX-0730795 | —CH(CH₃)₂ | 4-(methylthio)phenyl | 4-benzylpiperidin-1-yl |

TABLE 5-continued
Compounds based on the 5E core
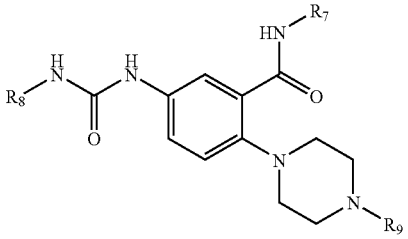
5E core
| Name | R<sub>7</sub> | R<sub>8</sub> | R<sub>9</sub> |
|---|---|---|---|
| CGX-0731125 | —(CH$_2$)$_5$ |  | —N(CH$_3$)$_2$ |
| CGX-00731278 | 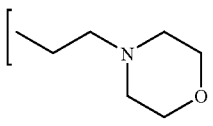 | 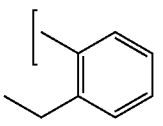 | 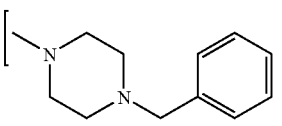 |
| CGX-0731359 | 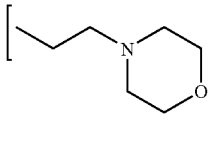 | 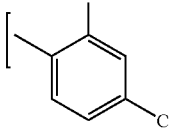 | 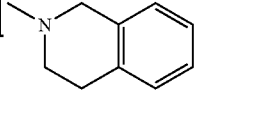 |
| CGX-0731462 | 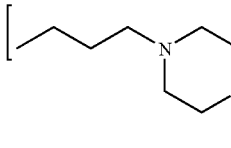 | 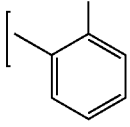 | 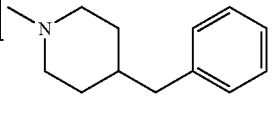 |
| CGX-0733464 | —CH$_2$CH(CH$_3$)$_2$ | 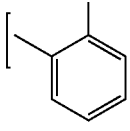 | 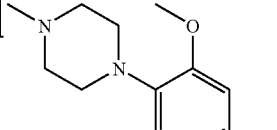 |
| CGX-0733818 | —(CH$_2$)$_5$ | 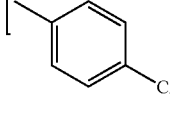 | 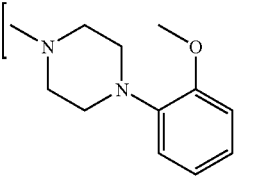 |
| CGX-0752302 | —CHCH$_3$CH$_2$CH$_3$ | —C(CH$_3$)$_3$ | 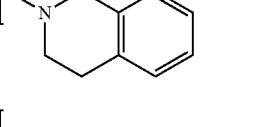 |
| CGX-0752382 | —(CH$_2$)$_5$ | 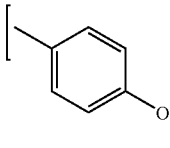 | 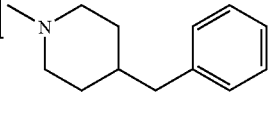 |

TABLE 5-continued

Compounds based on the 5E core 5E core

| Name | $R_7$ | $R_8$ | $R_9$ |
|---|---|---|---|
| CGX-3006045 | benzyl | 3-cyanophenyl | —N(CH$_3$)$_2$ |

Compounds identified in the above screens, and subsequent screens, can be tested any of the in vitro and in vivo assays described herein and known in the art, including the reporter cell screening assay, neurological protection assay, bioavailabilty assay, toxicity assay, ADMET (i.e., absorption, distribution, metabolism, and excretion) assays, blood-brain barrier assay, in vivo/transgenic animal assays, and behavioral assays, described above and in Examples.

The present compositions and methods include salts of active compounds and formulations containing active compounds.

V. Effects of TGF-β Analogs In Vitro

Some of the small-molecule TGF-β agonist compounds were tested for neuroprotection activity and toxicity in vitro (cell culture). In addition, the mechanism of action of the agonists was explored using cells with different genetic backgrounds with respect to protein of the TGF-β1 signaling pathway.

A. Neuroprotection Activity

FIG. 1H shows representative data from several experiments in which Aβ oligomers are used at different concentrations to induce 50-70% cell death in cultures of primary hippocampal neurons from E16 mouse embryos. TGF-β1 and a small molecule TGF-β agonist (13A04) consistently protected neurons and increased survival. Moreover, the small-molecule TGF-β agonist was not toxic at 3 μM and 10 μM (not shown). These results demonstrated that small-molecule TGF-β signaling agonists, such as 13A04, were active in primary neurons and protected them against Aβ toxicity.

B. Toxicity

A microarray assay was used to identify changes in gene expression caused by stimulating tgfb1$^{-/-}$ fibroblasts with TGF-β1 or 13A04. mRNA was harvested 1, 5, and 24 hours following stimulation of tgfb1$^{-/-}$ fibroblasts with TGF-β1 (or control) and analyzed for differential expression of 128 genes related to TGF-β signaling, using a commercially available filter array (Superarray Bioscience Corp.; FIG. 1I). While the expression of many genes was induced by TGF-β1 and 13A04 treatment (e.g., Fos, Jun, Myc, Smad1, Smad2, Smad3, Interleukin-6, etc.) the expression of other genes was differentially by TGF-β1 and 13A04 (e.g., Bmper, Col1a1, Fkbp1b, Serpine1 (aka PAI-1), Plat, etc.). Several genes in the latter group have important roles in vascular remodeling. These data suggest that 13A04 (and similar analogs) are agonists of the TGF-β signaling pathway, mimicking the actions of TGF-β1. However, there may be additional clinical advantages, e.g., involving vascular remodeling, of the small-molecule agonists.

C. Mechanism of Action/Targets

Figure 2:
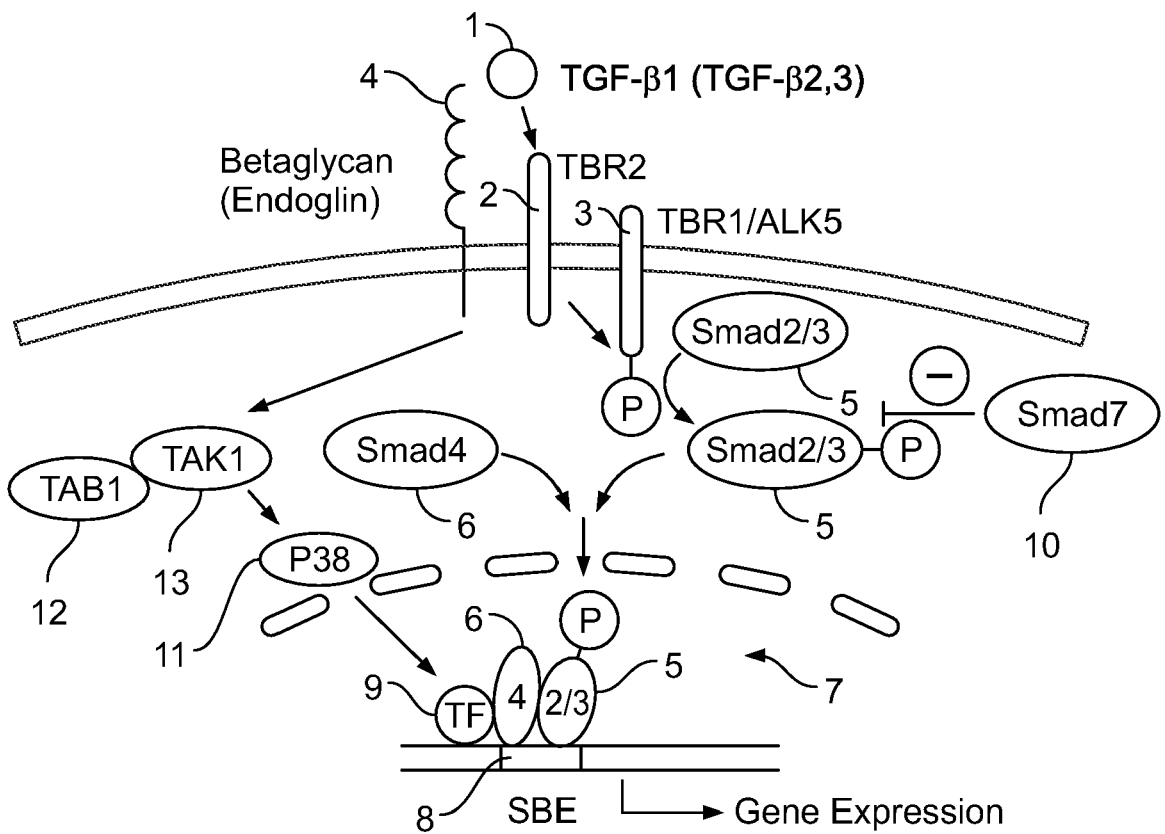
FIGS. 2A-2D show a model and results relating to screening a library of compounds. (A) Diagram of the TGF-β signaling pathway. (B-D) Graphs showing activity in transfected cells.
Figure 2:
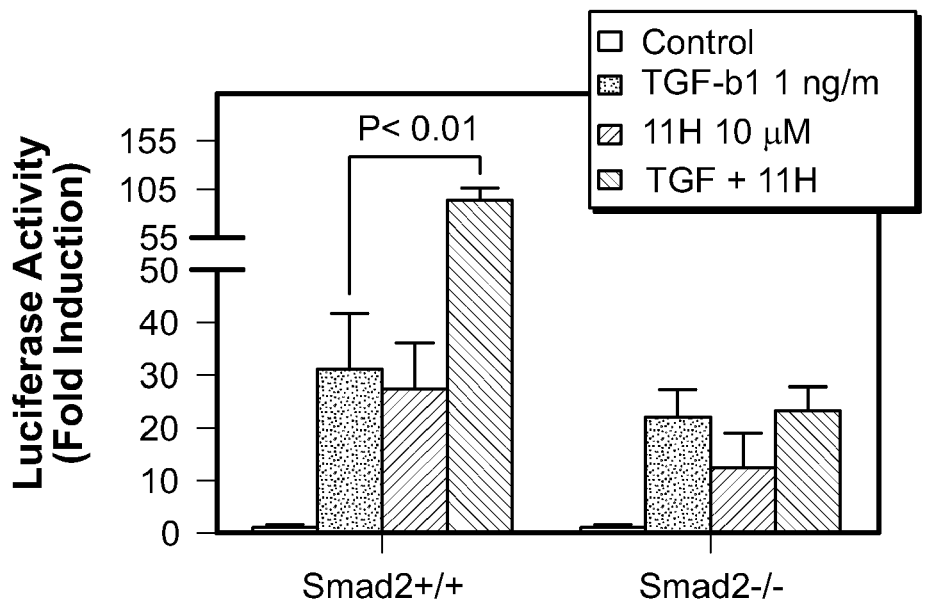
Figure 2:
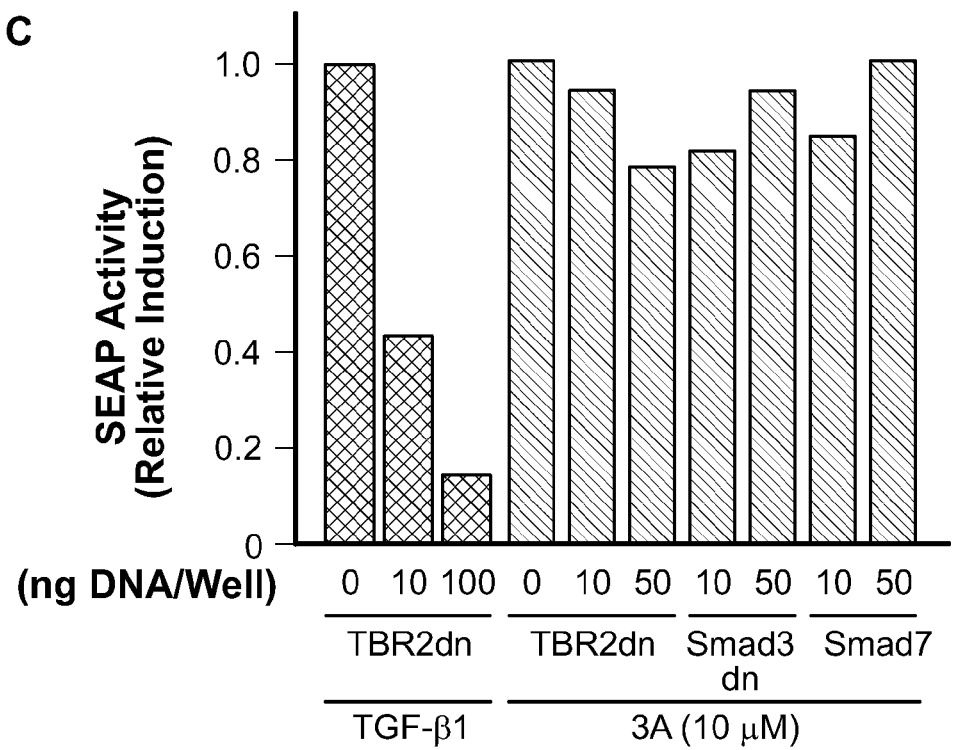
Figure 2:
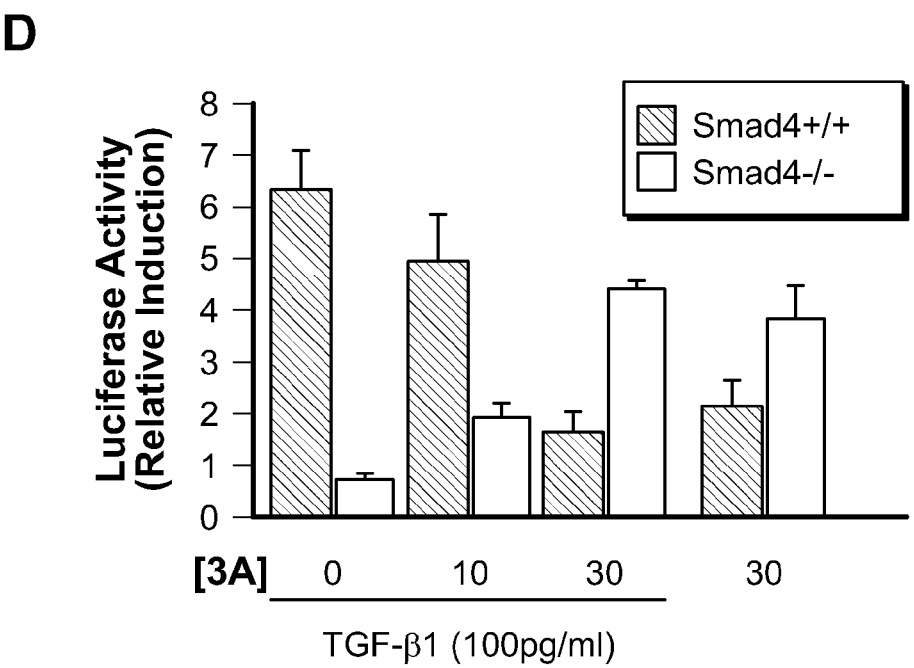

To understand how the TGF-β signaling agonists function and identify molecular genetic targets in cells, fibroblasts lacking different elements of the TGF-β signaling pathway, including Smad2, Smad3, and Smad4, were used in combination with plasmids encoding different inhibitors of the TGF-β signaling pathway to study TGF-β agonists in different backgrounds. For reference, the canonical TGF-β signaling pathway is illustrated in FIG. 2A. The biological actions of TGF-β1 are mediated through interactions with the type 2 TGF beta receptor (TBR2) 2 and the type I TGF beta receptor (TBRI) 3. Betaglycan 4 may participate in the binding of TGF-β1. Receptor activation leads to the phosphorylation of Smad proteins, such as Smad 2/3 5 and Smad 4 6, which translocate to the nucleus 7 to bind to the Smad, DNA-binding element (SBE) 8, present in numerous genes, in combination with transcription factors (TF) 9. Smad 7 10 is inhibitory with respect to Smad 2/3 5 phosphorylation. Alternative signaling involves p38 11 and the MAP kinase pathway. TAB1 12 activates TAK1 13, which activates p38 11.

The signaling of recombinant TGF-β1 is blocked or strongly inhibited by the absence of Smad4 or the expression of a dominant negative (dn) TGF-β receptor, dominant negative Smad 3, or Smad 7 (FIGS. 2B-2D). Signaling by the 3A agonist was not affected (or was even stronger) in the absence of Smad4 (FIG. 2D).

Because Smad2 and Smad3 can substitute for each other, results with Smad2 or Smad3 knock-out fibroblasts were more difficult to interpret. Nonetheless, the synergistic effect of TGF-β1 and 11H was blocked in the absence of Smad2 (FIG. 2B) or Smad3 (not shown). In these assays, signaling is reported via SBE elements, which are specific elements that bind Smad proteins. Thus, the 11H compound must signal through this element. Without being limited to theory, it is believed that the 3A compound functions as a competitive agonist of Smad binding to the SBE, representing a novel target and mode of action.

VI. Animal Studies

Transgenic mice harboring the SBE-luc reporter gene were generated and used to test the present compositions in vivo. These "reporter mice" mice express SBE-luc (i.e., "the transgene") in all cells of the body.[1,54] Intraperitoneal injection of luciferin into SBE-luc mice produces bioluminescence generated by luciferase and photons penetrating the skull can be imaged using sensitive camera systems.[1,54]

A. Monitoring TGF-β Pathway Activation in Animals

Tissue analysis of transgene expression at basal level in 2-month-old mice of lines T9-55 and T9-7 showed the highest levels of luciferase activity in the brain. Further dissection of the brain into different regions (not shown) demonstrated the highest levels of reporter activity in the hippocampus and cortex.

Primary astrocytes and primary neurons isolated from the brains of the SBE-luc mice showed increased expression of luciferase in response to recombinant TGF-β1.[1] Luciferase activation corresponded with nuclear translocation of activated (i.e., phosphorylated) Smad2, which is a transcription factor and downstream signal transducer of the TGF-β signaling pathway (not shown).

These experiments demonstrated that the reporter mice show the expected distribution of TGF-β1 in the body and that the mice responded as expected to exogenous TGF-β1. The transgene can be used to monitor activation of the TGF-β signaling pathway in vivo using living mice.

B. Bioactivity and Availability

Figure 3:
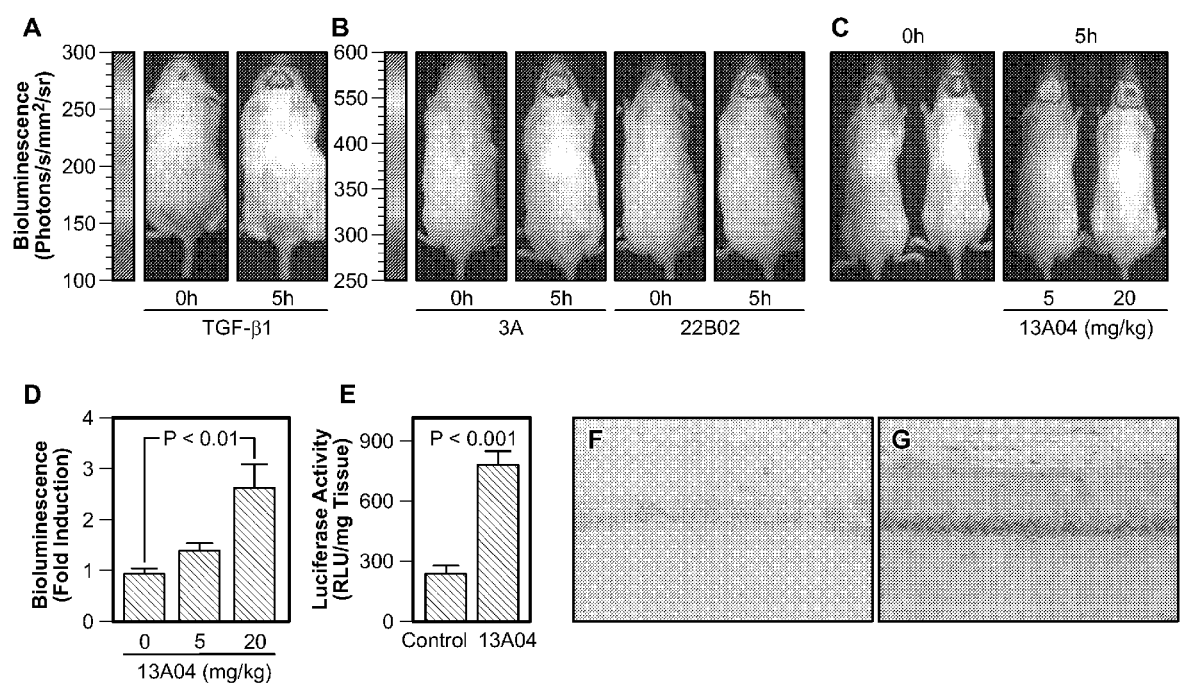
FIGS. 3A-3G show the results of experiments using transgenic reporter mice to monitor the activity of TGF-β and an exemplary TGF-β agonist. (A-C) Representative images of mice treated with the indicated drugs at baseline or 5 h after treatment. (D, E) Graphical representations of bioluminescence changes (fold-induction) following administration of an exemplary TGF-β analog.

To determine whether 3A and its analogs are bioactive in vivo and able to penetrate the blood brain barrier (BBB), TGF-β1, 3A, 22B02, or 13A04 were injected into reporter mice i.p. or s.q. The animals were then sacrificed at the indicated times following injection. Bioactivity was measured in living mice using bioluminescence as shown in FIGS. 3A-3C. FIG. 3D summarizes the data, and shows that activation by 13A04 was in a dose-dependent manner. There was no obvious activation of the reporter in other organs.

Bioactivity data were confirmed by biochemical measurements of tissue luciferase in hippocampal homogenates (FIG. 3E). The results showed that peripheral administration of recombinant TGF-β1 and 3A-like compounds activated TGF-β signaling in vivo, indicating that the compounds pass the BBB.

C. TGF-β Signaling at the Cellular Level

To study TGF-β signaling at the cellular level, additional reporter mice were generated, which express a fusion protein consisting of luciferase, red fluorescent protein (RFP), and thymidine kinase (TK) under control of the SBE promoter (i.e., SBE-lucRT mice). Using RFP immunohistochemistry, it was shown that a TGF-β agonist (compound 13A04) activates the reporter gene and TGF-β signaling in hippocampal neurons (FIGS. 3F and 3G). These data are consistent with previous data showing expression of phosphorylated Smad2 in the same neurons of unmanipulated or injured wild-type mice. No activation of TGF-β signaling was observed in the vasculature. These results demonstrated that the TGF-β agonist activated TGF-β signaling in neurons in vivo.

D. Activation of TGF-β Signaling in Response to Excitotoxic Injury

SBE-luc mice were further used for non-invasive monitoring of reporter activation in response to excitotoxic injury. The mice were lesioned with kainate in a model for excitotoxic injury (FIG. 4A-4D).[54] Excitotoxicity causes an excessive activation of glutamate receptors and subsequent $Ca^{++}$ influx in neurons. The resulting neuronal injury leads to an inflammatory response and oxidative stress that amplifies neuronal degeneration and death.[75] Excitotoxicity has been postulated to be responsible, not only for neuronal loss associated with seizures, traumatic and ischemic brain injury, and hypoxia,[76] but also for neuronal damage in Alzheimer's disease and other neurodegenerative disorders.[55]

Relative luciferase reporter activity was measured in kainate lesioned SBE-luc mice as bioluminescence over the skull and compared with postmortem neuropathological parameters). The relative number of photons emitted from the brain in lesioned animals correlated with biochemical measurements of luciferase activity in postmortem hippocampal samples (not shown).

Figure 4:
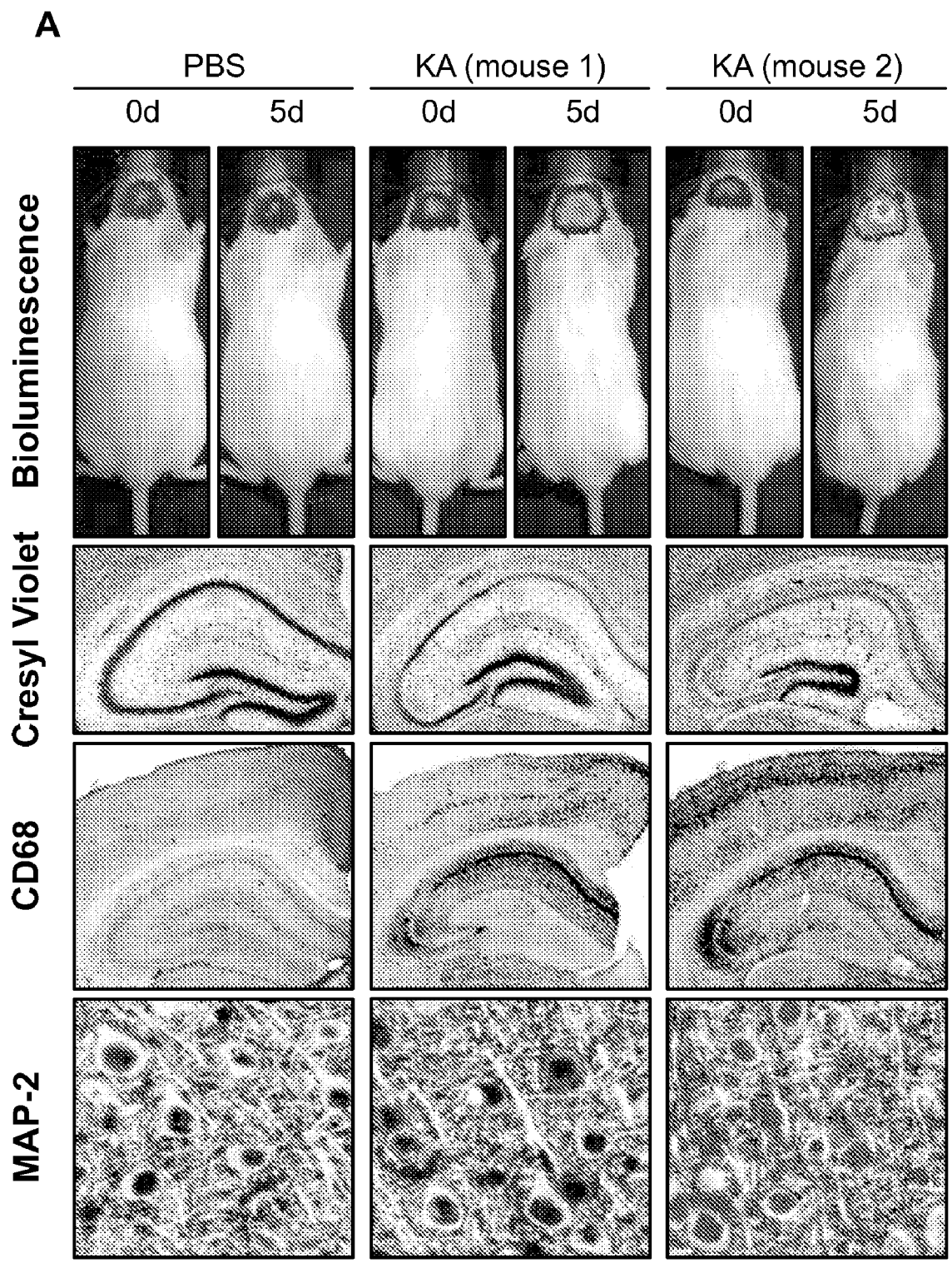
FIGS. 4A-4F show the results of experiments using reporter mice to monitor brain injury and drug efficacy and treatment of mice with an exemplary TGF-β agonist. (A) Images from sections of mice with different extent of injury and reporter gene activity. (B-E) Graphs relating to TGF-β activation by an exemplary TGF-β agonist. (F) Graph showing the results of Aβ immunohistochemistry.
Figure 4:
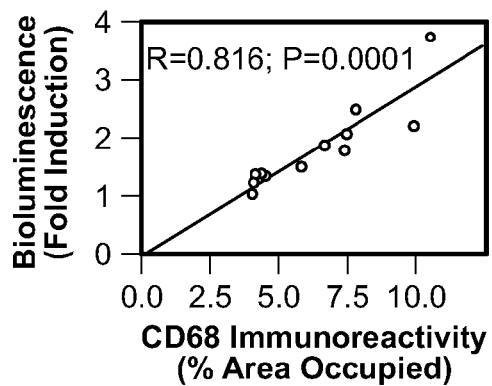
Figure 4:
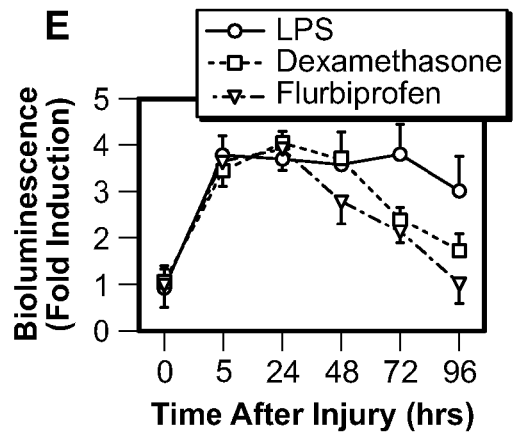
Figure 4:
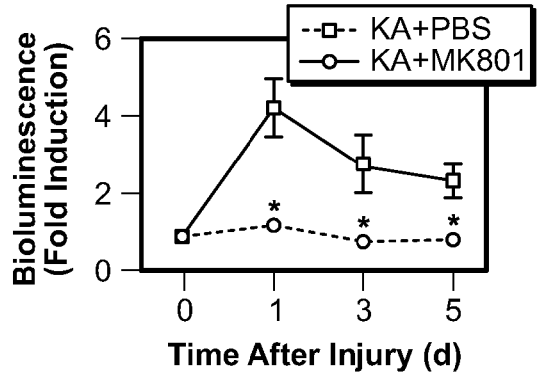
Figure 4:
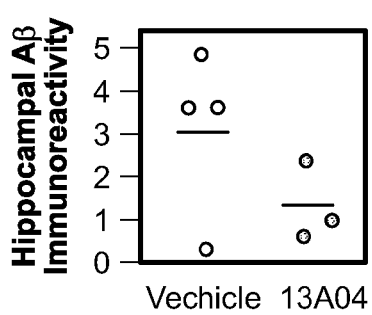
Figure 4:
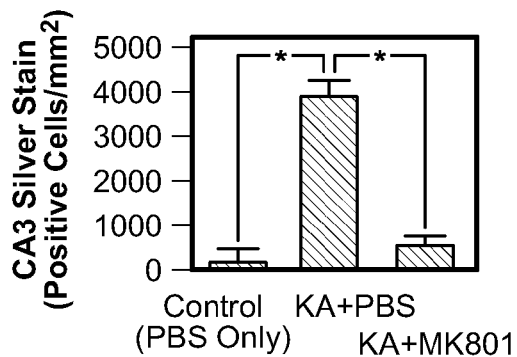

Neurodegeneration and microglial activation were most prominent in hippocampus and cortex although the extent of damage varied among mice. This variability is typical for kainate lesions and was advantages in correlating reporter gene activation with different degrees of damage. Bioluminescence corresponded to silver staining, which is a sensitive method for detecting degenerating cells as well as the relative number of pyramidal neurons estimated in cresyl violet-stained sections (FIG. 4A). Similar correlations were found with NeuN, MAP-2, synaptophysin, and calbindin immunostaining, which were used to assess synapto-dendritic and overall neuronal integrity.

Glial cells were sensitive to neuronal dysfunction and damage. Microglial activation measured as a function of macrosialin/CD68 expression showed highly significant positive correlations with bioluminescence (FIG. 4B). These data demonstrated that reporter gene activity correlated with neurodegeneration and microgliosis in kainate injured SBE-luc mice, further validating the animal model.

SBE-luc mice can also be used to monitor activation of TGF-β signaling in response to glial activation after lipopolysaccharide (LPS) administration. While LPS induces rapid and long-lasting activation of TGF-β signaling in the brain, treatment with anti-inflammatory drugs such as dexamethasone or flurbiprofen strongly reduced signaling (FIG. 4E) and microglial activation (data not shown). Bioluminescence imaging in living mice demonstrated the efficacy of these compounds in reducing signaling, validating the animal model.

In a further experiment, a group of 5-month-old APP-T41 mice were treated with vehicle or 13A04 (i.p.) for 10 days. At this age, the mice are starting to deposit Aβ which can be quantified in brain sections using Aβ immunostaining. The TGF-β agonist compound was well tolerated and no side effects were observed. Although the result were not statistically significant, a trend towards reduced Aβ deposition in 13A04-treated mice was observed, when compared with controls (FIG. 4F).

E. Activation of TGF-β Signaling in the Hippocampus

In another experiment performed to assess the ability of the present compounds to activate TGF-β signaling in animals, SBE-luc mice were given either PBS or the 11H compound via i.p. injections as described in Example 10. Following drug or PBS injection, mice were anesthetized with chloral hydrate and perfused with saline. Brains were dissected and snap-frozen. Hippocampal tissues were assayed for luciferase activity.

Hippocampi from mice injected with the 11H compound demonstrated twice the levels of activation of the TGF-β reporter gene compared to those injected with PBS (FIG. 1J), demonstrating the activity of the present compounds in increasing TGF-β signaling, in vivo.

VII. Summary of Results

Experiments performed in support of the present compositions and methods show that TGF-β1 is neuroprotective and can reduce the accumulation of Aβ in an animal model. Small-molecule agonists of TGF-β1 modulated TGF-β signaling and activated a reporter gene in the brains of transgenic mice. Together, these data suggest that agonists of the TGF-β signaling pathway can be used to reduce or prevent amyloid plaques and Aβ accumulation in the CNS, thereby treating or preventing Alzheimer's disease (AD) and associated diseases. While the present compositions and methods relate primarily to TGF-β1, one skilled in the art will recognize that TGF-β2 and β3 can be modulated in a similar manner.

While the present compositions and methods are described mainly for treatment and prevention of AD, other neurodegenerative diseases are characterized by amyloid plaques and/or accumulation of Aβ in the brain can be treated or prevented in a similar manner. Such diseases/disorders include localized amyloidosis while as well as systemic amyloidosis. Amyloidosis can appear without other pathology or can accompany plasma cell dyscrasia or multiple myeloma. Amyloidosis is also associated with chronic infection or chronic inflammation. Familial forms of amyloidosis include, familial Mediterranean fever (FMF), familial British dementia (FBD), and familial amyloid polyneuropathy (FAP). Another form of amyloidosis is found in long-term hemodialysis patients. Creuzfeldt-Jakob disease, motor neuron diseases, polyglutamine disorders (including Huntington's disease), progressive frontotemporal dementia (FTD), Lewy Body dementia (LB), progressive supranuclear Palsy (PSP), Pick's disease, and Parkinson's disease can also be associated with amyloid plaques and/or accumulation of Aβ in the brain.

Figure 8:
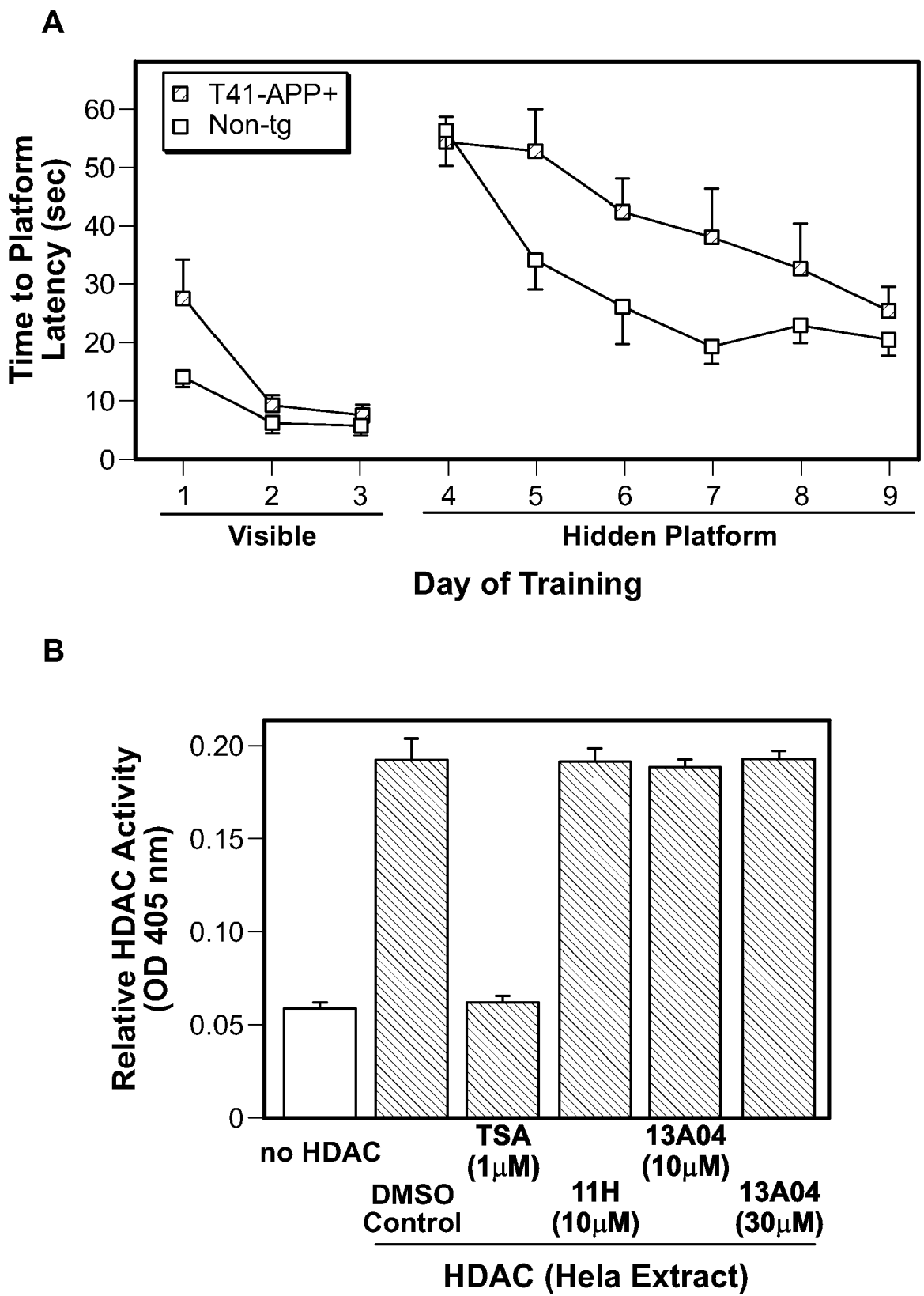
FIG. 8A is a graph showing the results of Morris water maze testing.
FIG. 8B is a graph relating to HDAC.

Chemical compounds with TGF-β agonist activity have previously been described (e.g., exemplified by A-161906 from Abbott Laboratories). Such compounds turned out to be hystone deacetylase (HDAC) inhibitors. A commercially available assay was used to measure HDAC inhibitory activity of the present small-molecule compounds. The present TGF-β agonists did not inhibit HDAC activity in HeLa nuclear extracts, while the known inhibitor, trichostatin A, reduced activity by >90% (FIG. 8B). Therefore the present compounds do not appear to be significant inhibitors of HDAC 1, HDAC 2, or SIRT 1 (the main HDACs tested in the assay). In contrast, the TGF-β agonist/HDAC inhibitor, A-161906 (Abbott), inhibited HDAC 1 and 2 with an IC50 of 9 nM.

VIII. Methods or Treatment

The present compositions are useful in the preparation of a medicament for treating or preventing diseases and conditions associated with reduced TGF-β signaling, including neurological disorders. In a particular example, the compositions are useful in treating or preventing AD or other diseases characterized by neurodegeneration. In some embodiments, the composition is provided in a pharmaceutical excipient suitable for oral delivery. In some embodiments, the composition is provided in a pharmaceutical excipient suitable for i.p., i.v., or i.m. delivery.

Tablets and capsules containing a compound for modulating the TGF-β pathway may be prepared by combining a compound with additives such as pharmaceutically acceptable carriers (e.g., lactose, corn starch, microcrystalline cellulose, sucrose), binders (e.g., alpha-form starch, methylcellulose, carboxymethylcellulose, hydroxypropylcellulose, hydroxypropylmethylcellulose, polyvinylpyrrolidone), disintegrating agents (e.g., carboxymethylcellulose calcium, starch, low substituted hydroxy-propylcellulose), surfactants (e.g., TWEEN® 80, polyoxyethylene polyoxypropylene copolymer), antioxidants (e.g., L cysteine, sodium sulfite, sodium ascorbate), lubricants (e.g., magnesium stearate, talc), or the like.

The present compounds can also be mixed with a solid, pulverulent or other carrier, for example lactose, saccharose, sorbitol, mannitol, starch, such as potato starch, corn starch, millopectine, cellulose derivative or gelatine, and may also include lubricants, such as magnesium or calcium stearate, or polyethylene glycol waxes compressed to the formation of tablets. By using several layers of the carrier or diluent, tablets operating with slow release can be prepared.

Liquid preparations for oral administration can be made in the form of elixirs, syrups or suspensions containing, e.g., ethanol, water, glycerol, propylene, glycol and possibly other additives of a conventional nature.

Other suitable formulations include a protective coating that protects the compound in the stomach and intestines until absorbed by the intestinal mucosa. Protective dosage forms for proteins are known in the art, and include enteric coatings and/or mucoadhesive polymer coatings. Exemplary mucoadhesive polymer formulations include ethyl cellulose, hydroxypropylmethylcellulose, Eudragit®, carboxyvinyl polymer, carbomer, and the like.

While the present compositions and methods have been described using particular experimental data and examples, further embodiments and uses of the compositions and methods will be apparent to the skilled artisan in view of the disclosure.

EXAMPLES

The following Examples are provided to illustrate the present compositions and methods and are in no way intended to be limiting.

Example 1

Iterative Reporter Cell Screen Assays

Compounds are tested for activation of the TGF-β signaling pathway using two different cell lines produced by stably transfecting cells with the SBE-SEAP reporter gene. These cells lines are TGF-β1 knockout fibroblasts MFB-F11 and mouse NG108-15 neuroblastoma cells. MFB-F11 cells do not produce TGF-β1 and are extremely sensitive to activators of the pathway.[53] Mouse NG108-15 neuroblastoma cells have been used extensively in the field (>1,100 references in Medline) because they can be differentiated into cells with neuron-like properties. Such cells are ideal for assaying TGF-β1 pathway activity in vitro.

Example 2

In Vitro ADMET Assays

Absorption, distribution, metabolism, and excretion (i.e., ADMET) assays, including metabolic stability assays using human liver microsomes, permeability assays modeling intestinal and blood brain barrier absorption, and drug interaction assays that evaluate cytochrome P450 inhibition, are known in the art[62,63] and can be used to evaluate any of the above compounds and those apparent in view of these compounds. Compounds that show favorable characteristics in these in vitro assays can be further evaluated for oral bioavailability and toxicity (maximum tolerated dose) in vivo.

Example 3

Neuroprotection Assays

Primary mixed neuronal cultures are exposed to Aβ oligomers and treated with compounds (0 to 10 μM concentration) and cell survival is measured using lactate dehydrogenase (LDH) release or by counting 4,6-diamidino-2-phenylindole (DAPI)-stained cells. Aβ oligomers may be produced according to a protocol described by LaDu and coworkers.[69] Such preparations contain mostly oliogomeric Aβ, as demonstrated using atomic force microscopy, and it is toxic to neurons. Neuritic dystrophy in 21 DIV neurons can also be measured by quantifying the tortuosity of neurites as described by Ferreira et al.[70] and modified by others. FIG. 1C shows the effect of Aβ on these cells. Further incubation of these cells with the present compounds provides a sensitive assay for neuroprotection.

Example 4

Bioavailability in Animals

Male Sprague-Dawley Rats

Oral bioavailability and BBB passage of test compounds can be measured using, e.g., male Sprague-Dawley rats. Animal brains are collected from rats at preselected times following administration of a test compound or control and a bioanalytical method, e.g., LC/MS-MS, is used to determine bioavailability by comparing the plasma level curves and the brain concentration of the parent drugs after, e.g., i.v. or oral administration. All data from these studies will be analyzed using WinNonlin (SCI Software, NC) or a similar software program to determine appropriate pharmacokinetic parameters such as terminal elimination half-life, area under the curve (AUC), maximum concentration in blood and/or plasma after oral administration ($C_{max}$), and other pharmacokinetic parameters as appropriate. These experiments will be used to determine the % bioavailability of compounds in plasma and brain and show which compounds are orally active and enter the blood.

SBE-Luciferase Transgenic Mice

Two-month old SBE-luciferase transgenic mice receive different concentrations of a test compound either s.q., i.p., or orally by gavage. Compound doses may be estimated from in vitro potency, and are typically in the range of from about 1 to about 50 mg/kg body weight. Following administration of the test or control compounds, mice are injected with luciferin i.p. At, e.g., 2, 8, and 16 hours following injection of luciferin, the mice are imaged to detect bioluminescence as described above. Brains may be harvested 16 hours following test compound injection, and may be divided sagittally. For example, one hemi-brain can be homogenized in luciferase assay buffer for measurement of reporter gene activation, while the other hemi-brain can be frozen at −70° C. for future study, including sectioning into individual brain regions.

Using this assay, compounds can be tested for the optimal route of injection, half-life, bioactivity, toxicity, efficiency of crossing the blood brain barrier (BBB), accumulation in particular regions of the brain, etc.

Example 5

Toxicity in Animals

Toxicity of test compounds can be determined in male and female Sprague-Dawley rats. Dose levels are estimated based on structure-activity analysis, comparison to toxicity of similar drugs, data obtained in vitro, and data obtained in other in vivo studies. A range of doses covering at least one log are typically employed. Three rats/sex/dose group are administered, e.g., a single oral or i.p. dose of test compound on Day 1 in an appropriate vehicle (e.g., water, methylcellulose, corn oil). In some examples, three dose levels are evaluated for each test compound, along with an appropriate control (e.g., vehicle). The rats are euthanized and necropsied on Day 5. Endpoints include daily clinical observations, body weights, clinical pathology and gross pathology at necropsy. These studies show whether compounds have unusual toxicity in a particular organ and help establish a maximal therapeutic dose.

Example 6

Excitotoxic Injury Model

Mice are injured with kainic acid and treated with different test compounds at two concentrations each to determine if they can reduce neurodegeneration and/or microglial activation. Wildtype mice on the FVB/N genetic background (8-weeks-old) will be injured with kainic acid (Tocris, Ellisville, Mo.) dissolved in PBS and injected subcutaneously (s.q., 20 mg/kg).[54] Seizure activity is scored from 0 to 5, with 0 corresponding to no behavioral changes and 5 corresponding to constant rearing and falling.[77] Only kainate-injected mice reaching at least stage 3 are used for the studies. On day five following injury, mice are anesthetized, transcardially perfused with 0.9% saline, and brains harvested and dissected. One hemi-brain may be fixed for 24 hours in 4% paraformaldehyde and cryoprotected in 30% sucrose. Serial coronal sections (40 μm) can be cut with a freezing microtome (Leica, Allendale, N.J.) and stored in cryoprotective medium. One set of sections, representing different levels of the hippocampus, will be used for the various stains. The other hemi-brain will be dissected into hippocampus, cortex, thalamus, brain stem, and cerebellum. In this manner, the ability of test compounds to reduce neurodegeneration in kainate-injected mice can be assayed.

Example 7

Bioluminescence In Vivo Imaging in Transgenic Reporter Mice

Bioluminescence has been used recently to monitor and quantify gene activity repeatedly in the same animal in vivo and to study disease progression in peripheral organs with great success.[46,47] Although, this imaging modality lacks high resolution and cannot be used at present to localize signals at the cellular level, it is quantitative and can faithfully report gene activation if appropriate fusion gene constructs are used. While initial studies demonstrated the use of this technology for the tracking of luciferase expressing bacteria or tumor cells in vivo,[46,47] more recently transgenic mice were generated that express the Firefly luciferase reporter gene under control the HIV-1 LTR[48], c-fos[49], or β-lactoglobulin,[50] or NF-kB promoters/enhancers.

Example 8

Transgenic APP-T41 and Prp-tau Mice

Transgenic mice that overproduce FAD-mutant human APP reproduce important aspects of AD, including amyloid plaques, neurodegeneration, and cognitive deficits. APP-T41 mice which overexpress APP751$^{V717I, K670M/N671L}$ in neurons develop amyloid pathology, neurodegeneration, and cognitive deficits.[43,44] Mice overexpressing human tau protein associated with familial forms of fronto-temporal dementia (a dementia characterized by extensive tangle formation) develop neurofibrillary tangles similar to the ones observed in AD and suffer from locomotor deficits around 10 months of age.[45] APP-T41 and Prp-tau$^{P301L}$ mice[45] can be used to determine the in vivo efficacy of test compounds in treating AD-like diseases.

APP-T41 mice have low but detectable levels of Aβ in brain and plasma at 2-months of age, consistently show Aβ deposits at 5-months of age, and exhibit a prominent pathology at 12-months of age.[43,44] Test compounds will be administered to animals at different stages of disease progression to determine when the compound should be administered for maximum effect, how late in disease progression compounds can be delivered, and the degree of protection afforded by the compounds. Compounds can also be tested for their ability to reverse cognitive deficits.

Prp-tau$^{P301L}$ mice show consistent tau pathology around 6-months of age and develop motor deficits around 9-months of age. Motor function can be tested using a rotarod and cognitive function can be tested using a fear conditioning paradigm.

Both short-term and long term studies can be performed using APP-T41 and Prp-tau$^{P301L}$ mice.

Example 9

Behavioral Analysis

Morris Water maze: Mice are trained on a Morris water maze as described[85]. Latency, path length, and proximity scores serve as measures of learning. A probe trial will be administered 1 and 7 days after training, followed by reversal trials to determine whether the observed results are due to behavioral inflexibility. Swim speeds will also be compared.

FIG. 8A shows data obtained in an exemplary Morris water maze experiment carried out in T41-APP mice. Half males and half females were tested in two stages: First, in visual platform training, mice swam to a platform marked with a black and white pole to train the mice to swim to the platform where they were subsequently rescued by the experimenter. Each mouse swam 4-times a day for 3 days. Second, in hidden platform training, 3-D visual cues were added to the walls of the facility, and the black and white pole removed. The mice were placed into the tank and swam around the tank to find the hidden platform (up to 90 seconds), using the cues to triangulate their position. Mice were left on the platform for 10 seconds at the end of the trial to remember the position of the platform (acquisition phase). Each mouse swam 4 times a day for 6 days. Significant differences in acquisition were detected at days 5, 6 and 7 using Student's t test and overall differences were significant with repeated measures ANOVA (p<0.006).

Contextual fear conditioning: To assess cognitive function in r™4510 tau mice a Pavlovian fear-conditioning paradigm can be used in addition to the water maze.[86-88] Briefly, after receiving a foot shock coupled with an acoustic stimulus in a brightly lit chamber, mice are exposed to the same chamber (contextual memory assessment) or placed in a differently shaped, scented, and lit box (cued memory assessment), e.g., 24 hours or 10 days later. The freezing response of the mice is then quantified. This type of memory test is reliable for assessing deficits in contextual memory and discreet cued memory in mice.[86,87] It involves a rapidly acquired form of learning, thought to be a model of human explicit memory that appears to involve the hippocampus and that is impaired in AD.[89] An additional advantage of fear conditioning over other spatial memory tasks, such as the Morris water maze, is that it minimally relies on motor skills (i.e. stamina and speed), or vision, and allows cognitive testing of mice with slight motor deficits, as is the case for some transgenic mice.

Example 10

Luciferase Activity in SBE-luc Mouse Hippocampus

SBE-luc mice (T9-7F), 24 months of age, 4-5 mice per group, were given either the 11H compound at 30 mg/kg via i.p. injections, or PBS as a control. The 11H compound was completely dissolved in PBS at the concentration of 3 mg/ml. This working solution was given to mice at 10 μl/g body weight to achieve the desired level of 30 mg/kg. Five hours following drug or PBS injection, mice were anesthetized with chloral hydrate and perfused with saline. Brains were dissected and snap-frozen. Hippocampal tissues were homogenized in 100 μl of 1× luciferase assay buffer and 20 μl of the resulting supernatant was used for luciferase assays.

Hippocampi from mice injected with the 11H compound demonstrated twice the levels of activation of the TGF-β reporter gene compared to those injected with PBS (FIG. 1J). These data indicated that the 11H compound specifically activated TGF-β reporter gene expression, and therefore, TGF-β signaling, in vivo.

What is claimed is:
1. A compound having the structure:

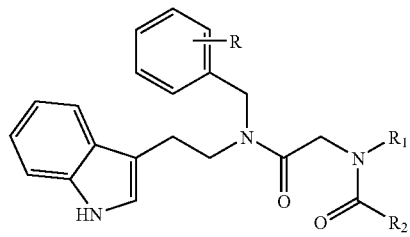

wherein

R is selected from the group consisting of H, p-CF$_3$, p-F, p-N(CH$_3$)$_2$, and o-OCH$_3$;

R$_1$ is selected from the group consisting of

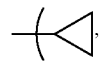

—CH(CH$_3$)$_2$, —CH$_2$CH(CH$_3$)$_2$, —CH$_2$N(CH$_3$)$_2$, and —(CH$_2$)$_{2\ or\ 3}$OCH$_3$; and R$_2$ is selected from the group consisting of

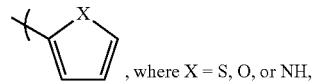, where X = S, O, or NH,

-continued

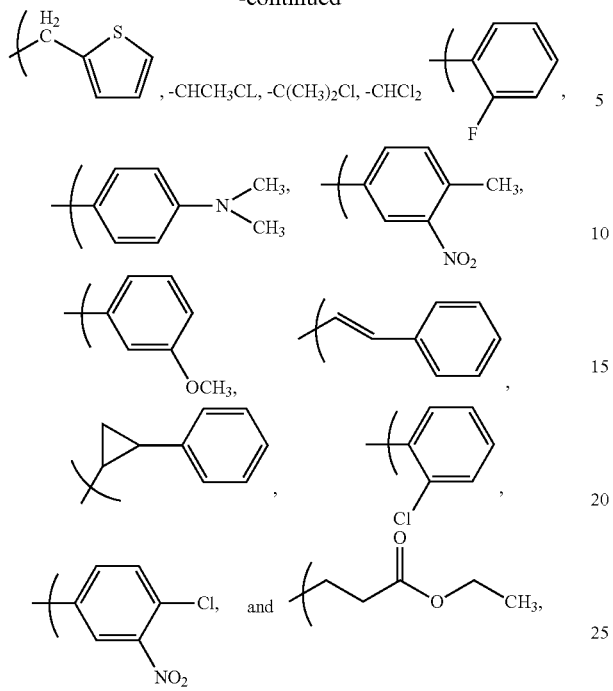

and salts thereof, where

in the foregoing structures indicates the point of attachment.

2. The compound of claim 1, wherein when R is equal to H, R$_1$ is selected from the group consisting of

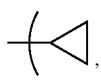

—CH$_2$CH(CH$_3$)$_2$, —CH$_2$N(CH$_3$)$_2$, and —(CH$_2$)$_2$OCH$_3$, and R$_2$ is selected from the group consisting of

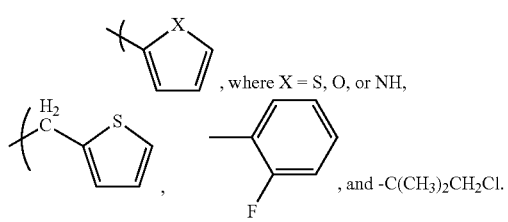

3. The compound of claim 1, wherein when R is p-CF$_3$, R$_1$ is selected from

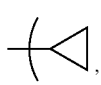

—CH(CH$_3$)$_2$, —CH$_2$CH(CH$_3$)$_2$, and —(CH$_2$)$_{2\ or\ 3}$OCH$_3$, and R$_2$ is selected from the group consisting of

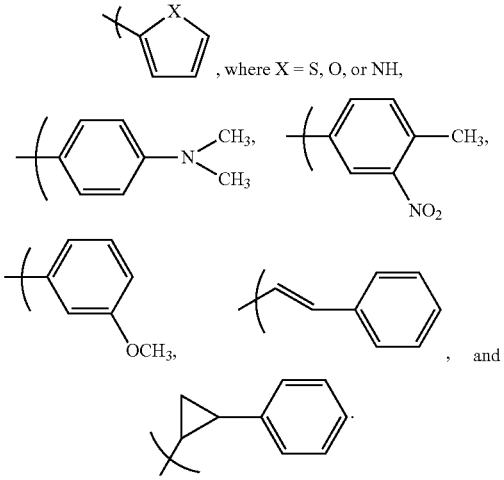

4. The compound of claim 1, wherein when R is p-F, R$_1$ is —(CH$_2$)$_{2\ or\ 3}$OCH$_3$ and R$_2$ is selected from —CHCH$_3$Cl,

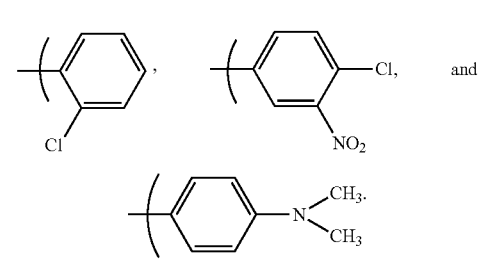

5. The compound of claim 1, wherein when R is p-N(CH$_3$)$_2$, R$_1$ is selected from —CH(CH$_3$)$_2$, —CH$_2$CH(CH$_3$)$_2$, and —(CH$_2$)$_2$OCH$_3$, and R$_2$ is selected from

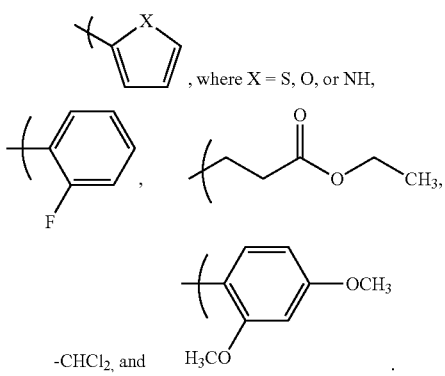

6. The compound of claim 1, wherein when R is o-OCH$_3$, R$_1$ is either

 or

—(CH$_2$)$_2$OCH$_3$, and R$_2$ is either

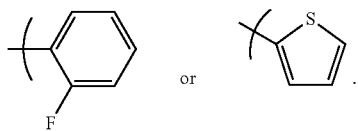

7. The compound of claim 1, wherein R is hydrogen, R$_1$ is —CH$_2$CH(CH$_3$)$_2$, and R$_2$ is

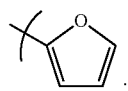

8. The compound of claim 1, wherein R$_1$ is —(CH$_2$)$_2$—OCH$_3$, R is hydrogen or p-CF$_3$, and R$_2$ is either

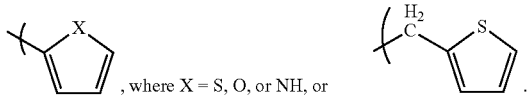

9. The compound of claim 1 corresponding to the structure,

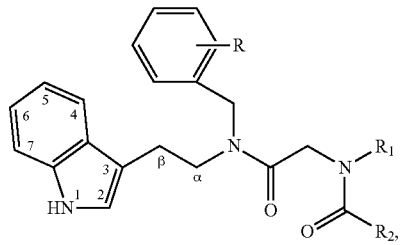

wherein the tryptamine is further substituted at one or more of the 4, 5, 6, or 7 positions, and wherein the substitution is independently selected, for each position, from the group consisting of fluoro, methyl, hydroxyl, methoxy, and benzyloxy.

10. The compound of claim 1 corresponding to the structure,

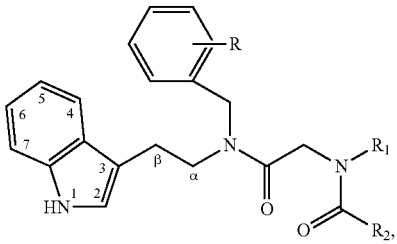

wherein the tryptamine is further substituted at one or more of the α or 1 positions, and wherein the substitution is independently selected, for each position, from the group consisting of fluoro, methyl, hydroxyl, methoxy, and benzyloxy.

11. The compound of claim 1 having the structure:

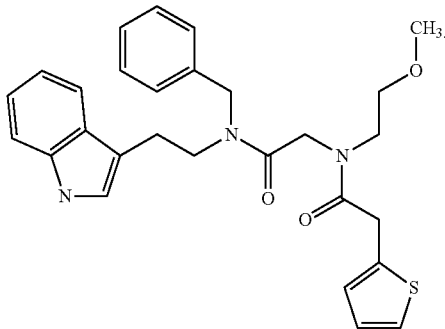

12. A pharmaceutical composition comprising a compound of claim 1 and an additive selected from the group consisting of pharmaceutically acceptable carriers, binders, disintegrating agents, surfactants, antioxidants, and lubricants.

13. The pharmaceutical composition of claim 12, in the form of a tablet, capsule, or a liquid for oral administration.

* * * * *

UNITED STATES PATENT AND TRADEMARK OFFICE
CERTIFICATE OF CORRECTION

| | | |
|---|---|---|
| PATENT NO. | : 8,097,645 B2 | Page 1 of 1 |
| APPLICATION NO. | : 12/249577 | |
| DATED | : January 17, 2012 | |
| INVENTOR(S) | : Wyss-Coray et al. | |

It is certified that error appears in the above-identified patent and that said Letters Patent is hereby corrected as shown below:

In the Specification:

• Please replace Column 1, line no. 12-18 with:

-- FEDERALLY-SPONSORED RESEARCH OR DEVELOPMENT
This invention was made with Government support under contract AG020603 awarded by the National Institutes of Health. The Government has certain rights in this invention. --

Signed and Sealed this
Twenty-seventh Day of August, 2013

Teresa Stanek Rea
*Acting Director of the United States Patent and Trademark Office*